US012778529B2

(12) United States Patent
Yamazoe et al.

(10) Patent No.: US 12,778,529 B2
(45) Date of Patent: Nov. 3, 2026

(54) IMAGE PROCESSING APPARATUS, IMAGE PROCESSING METHOD, AND COMPUTER-READABLE MEDIUM

(71) Applicant: CANON KABUSHIKI KAISHA, Tokyo (JP)

(72) Inventors: Manabu Yamazoe, Tokyo (JP); Atsushi Iwashita, Tokyo (JP); Ryuichi Fujimoto, Tokyo (JP); Osamu Sagano, Tokyo (JP); Ritsuya Tomita, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 590 days.

(21) Appl. No.: 18/168,599

(22) Filed: Feb. 14, 2023

(65) Prior Publication Data

US 2023/0263492 A1 Aug. 24, 2023

(30) Foreign Application Priority Data

Feb. 18, 2022 (JP) ................................ 2022-023949

(51) Int. Cl.
*A61B 6/00* (2024.01)
*A61B 6/02* (2006.01)
(Continued)

(52) U.S. Cl.
CPC ................ *A61B 6/482* (2013.01); *A61B 6/02* (2013.01); *A61B 6/505* (2013.01); *G06T 5/60* (2024.01);
(Continued)

(58) Field of Classification Search
CPC ......... A61B 6/482; A61B 6/5258; G06T 5/50; G06T 5/70; G06T 2207/10072;
(Continued)

(56) References Cited

U.S. PATENT DOCUMENTS

| | | | |
|---|---|---|---|
| 9,035,265 | B2 | 5/2015 | Yagi et al. |
| 9,239,390 | B2 | 1/2016 | Sato et al. |

(Continued)

FOREIGN PATENT DOCUMENTS

| | | | |
|---|---|---|---|
| JP | 2008167949 | A | 7/2008 |
| JP | 2011206367 | A | 10/2011 |

(Continued)

OTHER PUBLICATIONS

"Tradeoffs in CT Image Quality and Dose" by M.F. NcNitt-Gray. Medical Physics. 2006 (Year: 2006).*

(Continued)

*Primary Examiner* — Jason M Ip
(74) *Attorney, Agent, or Firm* — Carter, DeLuca & Farrell LLP

(57) ABSTRACT

An image processing apparatus is provided that includes: an obtaining unit configured to obtain a plurality of images relating to different radiation energies; and a generating unit configured to generate at least one of energy-subtraction images based on the plurality of images using a learned model, wherein the learned model is obtained using a first image obtained using a radiation and a second image obtained by improving image-quality of the first image or by adding a noise which has been artificially calculated to the first image.

6 Claims, 16 Drawing Sheets

(51) Int. Cl.
*A61B 6/50* (2024.01)
*G06T 5/60* (2024.01)

(52) U.S. Cl.
CPC ............... *G06T 2207/10072* (2013.01); *G06T 2207/20084* (2013.01); *G06T 2207/30008* (2013.01)

(58) Field of Classification Search
CPC . G06T 2207/20084; G06T 2207/10116; G06T 2207/20081; G06T 2207/20224
See application file for complete search history.

(56) References Cited

U.S. PATENT DOCUMENTS

| | | | | |
|---|---|---|---|---|
| 9,360,562 | B2 | 6/2016 | Sato et al. | |
| 9,417,333 | B2 | 8/2016 | Sato et al. | |
| 9,910,169 | B2 | 3/2018 | Iwashita et al. | |
| 10,234,574 | B2 | 3/2019 | Iwashita et al. | |
| 11,422,098 | B2 | 8/2022 | Iwashita et al. | |
| 2014/0320685 | A1 | 10/2014 | Takenaka et al. | |
| 2019/0156524 | A1* | 5/2019 | Park | G06T 5/60 |
| 2020/0408933 | A1 | 12/2020 | Iwashita et al. | |
| 2021/0104313 | A1 | 4/2021 | Mizobe et al. | |
| 2021/0158525 | A1 | 5/2021 | Iwase et al. | |
| 2021/0183019 | A1 | 6/2021 | Uchida et al. | |
| 2021/0224957 | A1 | 7/2021 | Iwase et al. | |
| 2021/0224997 | A1 | 7/2021 | Kushida et al. | |
| 2021/0304363 | A1 | 9/2021 | Makihira et al. | |
| 2021/0390696 | A1 | 12/2021 | Iwase et al. | |
| 2022/0107378 | A1* | 4/2022 | Dey | G06N 3/09 |
| 2022/0365004 | A1 | 11/2022 | Iwashita et al. | |
| 2023/0394630 | A1* | 12/2023 | Bergner | G06T 5/70 |

FOREIGN PATENT DOCUMENTS

| | | | |
|---|---|---|---|
| JP | 2020005918 | A | 1/2020 |
| JP | 2020099667 | A | 7/2020 |
| JP | 2020203083 | A | 12/2020 |
| JP | 2022013679 | A | 1/2022 |

OTHER PUBLICATIONS

Notice of Reasons for Refusal issued by the Japanese Patent Office on Mar. 3, 2026 in corresponding JP Patent Application No. 2022-023949, with English translation.

* cited by examiner

IMAGE PROCESSING APPARATUS, IMAGE PROCESSING METHOD, AND COMPUTER-READABLE MEDIUM

BACKGROUND OF THE INVENTION

Field of the Invention

The present disclosure relates to an image processing apparatus, an image processing method, and a computer-readable medium.

Description of the Related Art

Generally, spectral imaging of a time-division type is known as one of imaging technique. In the spectral imaging of the time-division type, a subject is irradiated with a plurality of radiations having different average energies in a short period of time, and the constituent materials of the subject are discriminated by measuring a rate at which the radiation of each average energy transmitted through the subject reaches a radiation measuring surface. Such spectral imaging of the time-division type has also been used to generate a medical radiation image.

The spectral imaging of the time-division type requires a plurality of imaging of the same site in a short period of time. Therefore, if the same site is imaged repeatedly with a dose which is equivalent to a dose used in a normal imaging, an amount of exposure of the subject is increased. Although the number of required images depends on a purpose of material decomposition, the spectral imaging of the time-division type requires a minimum of two images, and the exposure dose of the subject simply increases by the number of images. In order to reduce the increase of the exposure dose of the subject, it is possible to reduce the exposure dose per one image by reducing the dose of the radiation. However, if the dose of the radiation is reduced, the intensity of a noise increases and the image-quality of each image decreases.

In Japanese Patent Application Laid-Open No. 2020-5918, a method to reduce a noise by combine a high-frequency component of an average image obtained by combining a plurality of images obtained by irradiating radiations with different energies and a low-frequency component of each of the plurality of images. However, in the technique described in Japanese Patent Application Laid-Open No. 2020-5918, since different energy images are averaged, it is difficult to reduce the original noise of individual energy images.

An embodiment of the present disclosure has an object to provide an image processing apparatus that can generate at least one of energy-subtraction images with high image-quality while reducing a radiation dose used for examination.

SUMMARY OF THE INVENTION

An image processing apparatus according to an embodiment of the present disclosure comprises: an obtaining unit configured to obtain a plurality of images relating to different radiation energies; and a generating unit configured to generate at least one of energy-subtraction images based on the plurality of images using a learned model, wherein the learned model is obtained using a first image obtained using a radiation and a second image obtained by improving image-quality of the first image or by adding a noise which has been artificially calculated to the first image.

Further features of the present invention will become apparent from the following description of exemplary embodiments with reference to the attached drawings.

DESCRIPTION OF THE EMBODIMENTS

Figure 1:
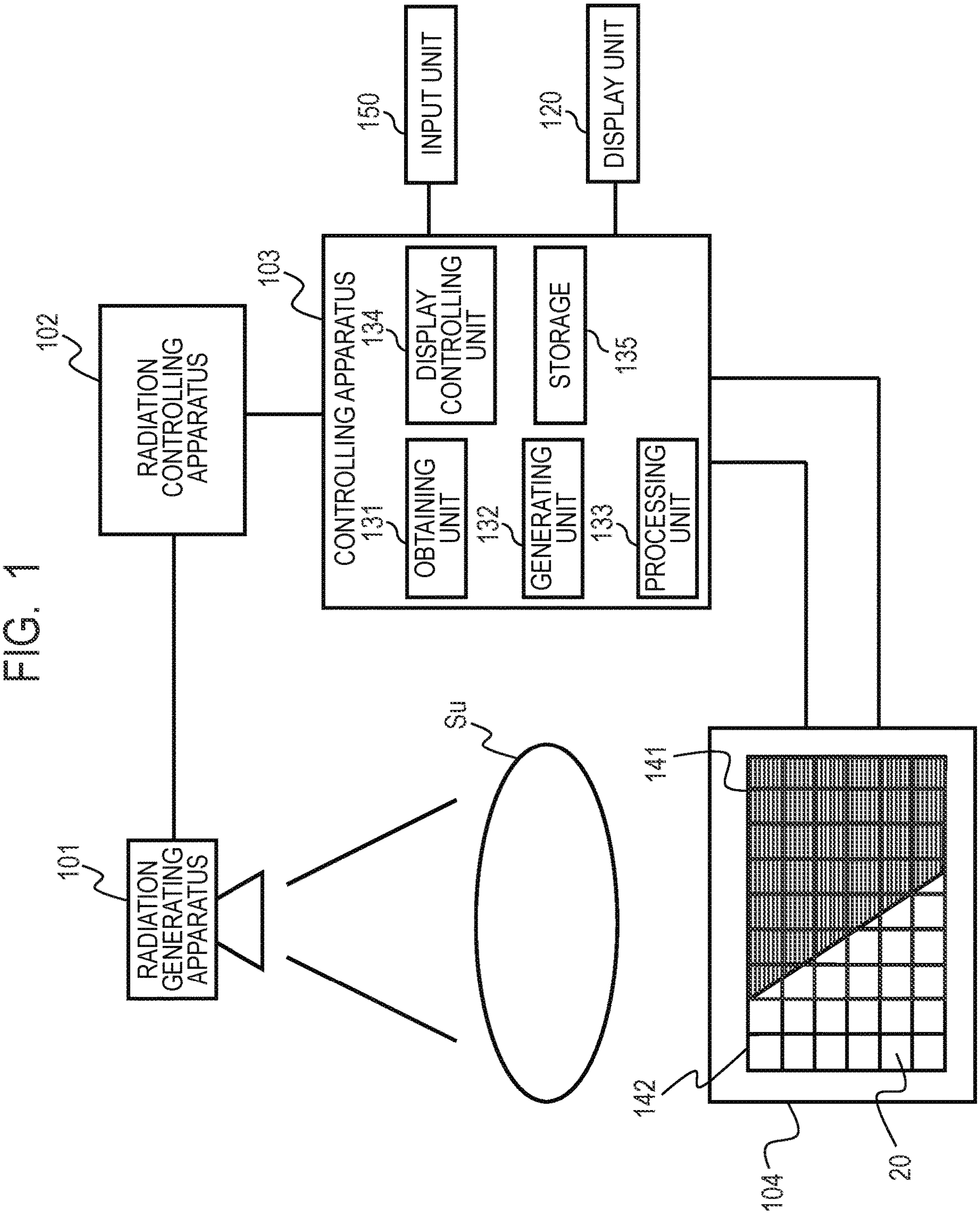
FIG. 1 is a diagram for illustrating an example of the overall configuration of a radiation imaging system according to a first embodiment.

Exemplary embodiments of the present invention will now be described in detail in accordance with the accompanying drawings.

However, the dimensions, materials, shapes, and relative positions of the components described in the following embodiment are not determinate, and can be changed according to a configuration of an apparatus to which the present invention is applied or various conditions. Further, in the drawings, identical or functionally similar elements are denoted by the same reference numerals in different drawings.

In the following embodiment, the term radiation can include X-rays as well as, for example, alpha rays, beta rays, gamma rays, particle rays and cosmic rays.

Further, the term "energy-subtraction processing" refers to processing in which images of different radiation energies (energy image) are used to obtain a difference thereof and obtain, for example, material decomposition images of bone and soft tissue or a contrast medium and water, information of an effective atomic number and area density, etc. Note that the energy-subtraction processing may include, for example, correction processing such as offset correction processing which is a pre-processing and image processing such as contrast adjustment processing which is a post-processing.

The term "energy-subtraction image" may include, for example, a material decomposition image obtained using the energy-subtraction processing, images indicating an effective atomic number and area density obtained using the energy-subtraction processing, and images obtained by improving the image-quality of those images. Further, the term "energy-subtraction image" may include material decomposition images and the like, which are inversely transformed from virtual monochromatic images of different energies. Furthermore, in the following embodiments, the term "energy-subtraction image" may include images obtained using the energy-subtraction processing as described above, and image inferred using a learned model obtained by training images inversely transformed from the virtual monochromatic images.

Further, hereunder, the term "machine learning model" refers to a learning model that learned according to a machine learning algorithm. Specific examples of algorithms for machine learning include the nearest-neighbor method, the naive Bayes method, the decision tree, and the support vector machine. The algorithms also include those for deep learning, which uses a neural network to generate a feature amount for learning and connection weight coefficients on its own. Algorithms that can be utilized among the aforementioned algorithms can be appropriately used and applied to the embodiments and modifications that are described hereunder. Further, the team "teacher data" refers to training data, and includes pairs of input data and output data. Further, the term "ground truth" refers to output data of training data (teacher data).

The term "learned model" refers to a model which has performed training (learning), with respect to a machine learning model that is in accordance with any machine learning algorithm, such as deep learning, using appropriate training data (teacher data) in advance. However, although the learned model is a model obtained using appropriate training data in advance, the learned model is not a model that does not perform further learning, and is a model that can also perform incremental learning. Incremental learning can also be performed after the apparatus is installed at the usage destination. Note that obtaining output data from input data by the learned model may be referred as "inferring".

First Embodiment

At present, a radiation imaging apparatus using a flat panel detector (FPD) including semiconductor materials is popular as an imaging apparatus for medical image diagnosis and non-destructive examination by a radiation. Such a radiation imaging apparatus is used as a digital imaging apparatus for performing still image capturing like general imaging and moving image capturing like fluoroscopic imaging in, for example, the medical image diagnosis. Generally, in the FPD, an integral sensor that measures the total amount of charges generated by incident radiation quanta is used for detecting a radiation. A noise that appears in the image captured in this manner is caused by a quantum noise according to fluctuation in the number of photons and an electrical noise generated by an electrical circuit used to read a signal.

In a case where spectral imaging of time-division type is performed, it is necessary to perform continuous imaging of the same site of the object to be examined in a very short time. In order to suppress the quantum noise to the intensity similar to that of normal imaging, it is necessary to irradiate a radiation dose equivalent to that of a normal imaging for each of images obtained by the continuous imaging. Therefore, in the medical field, the exposure dose of a subject to be examined increases in proportion to the number of captured images.

For the images obtained by the continuous imaging, since each of radiations with different average energies is irradiated, the transmittance of the radiation in the subject differs for each material and the contrast of each image is different from each other. However, since the images are captured in a short period of time, the shape of the subject in the images is almost the same. Therefore, by utilizing the fact that the shape of the subject is the same among the plurality of images, an energy-subtraction image such as a material decomposition image can be generated by performing energy-subtraction processing using the plurality of images. However, it is known that the noise increases when the material discrimination (decomposition) or the like is performed by the energy-subtraction processing.

Therefore, the first embodiment of the disclosure, by using a learned model (image-quality improving model) that outputs an image with high image-quality, generates at least one of energy-subtraction images in which the effect of noise is reduced while reducing the exposure dose to the subject to be examined. An image processing apparatus and an image processing method used in a radiation imaging system according to the first embodiment will be described below with reference to FIG. 1 to FIG. 10. Note that a medical radiation imaging system in which the object to be examined is a human body is described in the first embodiment. However, the technology according to the first embodiment can also be applied to an industrial radiation imaging system in which the object to be examined is a substrate, etc.

FIG. 1 is a diagram for illustrating an example of the overall configuration of the radiation imaging system according to the first embodiment. The radiation imaging system of the present embodiment includes a radiation generating apparatus 101 including a radiation source, a radiation controlling apparatus 102, a controlling apparatus 103, a radiation imaging apparatus 104, an input unit 150, and a display unit 120.

The radiation generating apparatus 101 includes a radiation source such as a radiation tube. The radiation generating apparatus 101 generates a radiation under the control by the radiation controlling apparatus 102. The radiation controlling apparatus 102 includes a control circuit, a processor, etc. The radiation controlling apparatus 102 controls the radiation generating apparatus 101 to irradiate the radiation toward the subject to be examined Su and the radiation imaging apparatus 104 based on the control of the controlling apparatus 103. More specifically, the radiation controlling apparatus 102 can control an imaging-condition, such as an irradiation angle of the radiation, a radiation focus, a tube voltage, and a tube current of the radiation generating apparatus 101.

The radiation controlling apparatus 102, the radiation imaging apparatus 104, the input unit 150, and the display unit 120 are connected to the controlling apparatus 103, and the controlling apparatus 103 can control them. The controlling apparatus 103 can perform, for example, various controls related to the radiation imaging and image processing for the spectral imaging.

The controlling apparatus 103 includes an obtaining unit 131, a generating unit 132, a processing unit 133, a display controlling unit 134, and a storage 135. The obtaining unit 131 can obtain images captured by the radiation imaging apparatus 104 and images generated by the generating unit 132. The obtaining unit 131 can also obtain various images from an external apparatus (not shown) connected to the control unit 103 via a network such as the Internet.

The generating unit 132 can generate a radiation image from an image (image information) captured by the radiation imaging apparatus 104, which is obtained by the obtaining unit 131. The generating unit 132 can generate, for example, energy images (high-energy image and low-energy image) relating to different radiation energies from images captured by the radiation imaging apparatus 104 which is irradiated with the radiation of different energies. The method of generating the energy images will be described later.

The processing unit 133 generates energy-subtraction images with high-image-quality based on the energy images of different energies by using the image-quality improving model. The generation method of image-quality improving model and energy-subtraction images will be described later. The processing unit 133 can perform image processing and analysis processing using the generated energy-subtraction images, etc. Further, the processing unit 133 can serve as an example of a learning unit performing training of the image-quality improving model.

The display controlling unit 134 can control a display of the display unit 120 and cause the display unit 120 to display, for example, information on the subject to be examined Su (object to be examined), information on radiation imaging, the obtained various images, the generated various images, etc. The storage 135 can store, for example examiner, the information on the subject to be examined Su, the information on the radiation imaging, the obtained various images, the generated various images, etc. The storage 135 can also include programs for performing various processing by the controlling apparatus 103, etc.

The controlling apparatus 103 may be configured by a computer including a processor and a memory. The controlling apparatus 103 can be configured by a general computer or a computer dedicated to the radiation controlling system. For example, a personal computer, and a desktop PC, a laptop PC, a tablet PC (a portable information terminal), or the like may be used for the controlling apparatus 103. Further, the controlling apparatus 103 can be configured as a cloud-type computer in which some components are arranged in an external apparatus.

Each component of the controlling apparatus 103 other than the storage 135 may be configured by software modules executed by a processor such as a CPU (Central Processing Unit) or an MPU (Micro Processing Unit). The processor may be, for example, a GPU (Graphical Processing Unit), an FPGA (Field-Programmable Gate Array), or the like. Each such component may be configured by a circuit or the like which serves a specific function, such as an ASIC. The storage 135 may be configured by, for example, an optical disk such as a hard disk or any storage medium such as a memory.

The display unit 120 is configured using any monitor, and displays various information, such as the information of the subject to be examined Su, various images, a mouse cursor according to the operation of input unit 150 and the like, according to the control by the display controlling unit 134. The input unit 150 is an input device that provides an instruction to the control unit 103, and specifically includes a keyboard and a mouse. Note that the display unit 120 may be configured with a touch-panel display, in which case the display unit 120 can also be used as the input unit 150.

The radiation imaging apparatus 104 detects a radiation irradiated from the radiation generating apparatus 101 and transmitted through the subject to be examined Su, and images the radiation image. The radiation imaging apparatus 104 can be configured, for example, as the FPD. The radiation imaging apparatus 104 includes a scintillator 141 that converts the radiation into visible light and a two-dimensional detector 142 that detects the visible light. The two-dimensional detector 142 includes a sensor in which pixels 20 for detecting radiation quanta are arranged in an array of X columns×Y rows, and outputs the image information according to the detected radiation dose.

Figure 2:
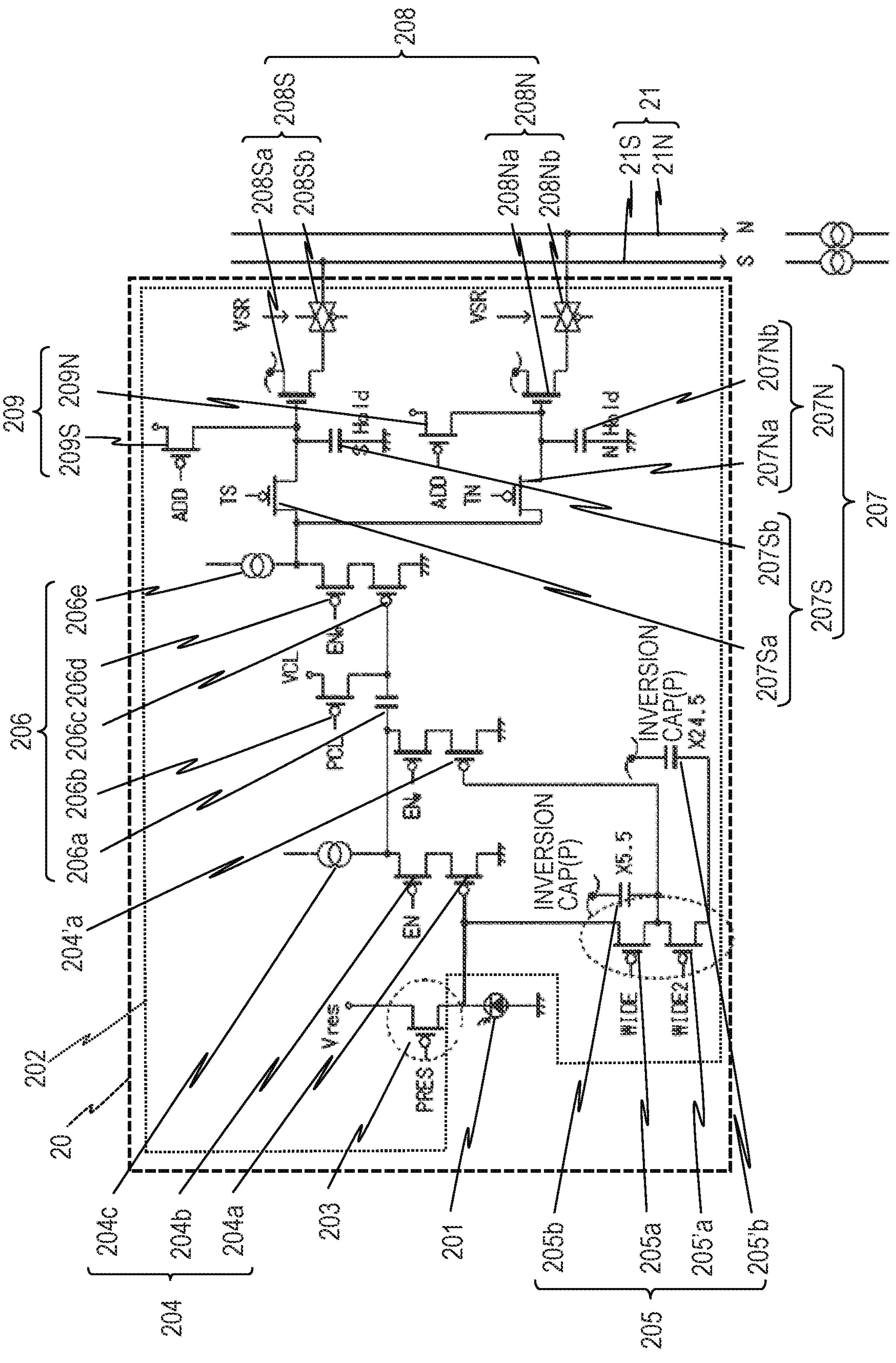
FIG. 2 is an equivalent circuit diagram of one example of a pixel of a radiation imaging apparatus according to the first embodiment.

An example of the pixel 20 will be described here with reference to FIG. 2. FIG. 2 is an equivalent circuit diagram of the example of the pixel 20. The pixel 20 includes a photoelectric conversion element 201 and an output circuit portion 202. The photoelectric conversion element 201 can typically include a photodiode. The output circuit portion 202 includes an amplifier circuit portion 204, a clamp circuit portion 206, a sample-and-hold circuit portion 207, and a selection circuit portion 208.

The photoelectric conversion element 201 includes a charge accumulation portion which is connected to the gate of a MOS transistor **204*a* of the amplifier circuit portion 204. The source of the MOS transistor 204*a* is connected to a current source 204*c* via a MOS transistor 204*b*. A source follower circuit is configured by the MOS transistor 204*a* and the current source 204*c*. The MOS transistor 204*b* is an enable switch that turns on when the enable signal EN supplied to the gate of the MOS transistor 204*b*** becomes the active level, and bringing the source follower circuit into an operating state.

In the example shown in FIG. 2, the charge accumulation portion of the photoelectric conversion element 201 and the gate of the MOS transistor 204*a* configure a common node. This node functions as a charge-voltage conversion portion that converts the charge accumulated in the charge accumulation portion of the photoelectric conversion element 201 into a voltage. The voltage V (=Q/C) determined by the charge Q accumulated in the charge accumulation portion and the capacitance value C of the charge-voltage conversion portion appears in the charge-voltage conversion portion. The charge-voltage conversion portion is connected to the reset electrical potential Vres via a reset switch 203. When the reset signal PRES becomes the active level, the reset switch 203 is turned on, and the potential of the charge-voltage conversion portion is reset to the reset electrical potential Vres.

The clamp circuit portion 206 clamps a noise output by the amplifier circuit portion 204 according to the reset electrical potential of the charge-voltage conversion portion, by the clamp capacitance 206*a*. That is, the clamp circuit portion 206 is a circuit for canceling the above-mentioned noise from the signal output from the source follower circuit according to the charge generated by the photoelectric conversion in the photoelectric conversion element 201. This noise includes a kTC noise at the time of the reset. The clamping is performed by bringing the clamp signal PCL to the active level and turning the MOS transistor 206*b* on, and then bringing the clamp signal PCL to the inactive level and turning the MOS transistor 206*b* off. The output side of the clamp capacitor 206*a* is connected to the gate of a MOS transistor 206*c*. The source of the MOS transistor 206*c* is connected to the current source 206*e* via a MOS transistor 206*d*. A source follower circuit is configured by the MOS transistor 206*c* and a current source 206*e*. The MOS transistor 206*d* is an enable switch that turns on when the enable signal ENO supplied to the gate of the MOS transistor 206*d* becomes the active level, bringing the source follower circuit into an operating state.

The signal output from the clamp circuit portion 206 according to the charge generated by the photoelectric conversion of the photoelectric conversion element 201 is written as an optical signal to a capacitor 207Sb via a switch 207Sa when the optical signal sampling signal TS becomes the active level. The signal output from the clamp circuit portion 206 when the MOS transistor 206*b* is turned on immediately after the electrical potential of the charge-voltage conversion portion is reset is the clamp voltage. The clamp voltage is written as a noise into a capacitor 207Nb via a switch 207Na when the noise sampling signal TN becoming the active level. This noise includes an offset component of the clamp circuit portion 206. A signal sample-hold circuit 207S is configured by the switch 207Sa and the capacitance 207Sb. A noise sample-hold circuit 207N is configured by the switch 207Na and the capacitance 207Nb. A sample-hold circuit portion 207 includes a signal sample-hold circuit 207S and a noise sample-hold circuit 207N.

When a driving circuit portion drives a row selection signal to the active level, the signal (optical signal) held by the capacitor 207Sb is output to a signal line 21S via a MOS transistor 208Sa and a row selection switch 208Sb. At the same time, the signal (noise) held by the capacitor 207Nb is output to a signal line 21N via a MOS transistor 208Na and a row selection switch 208Nb. A source follower circuit is configured by the MOS transistor 208Sa and a constant current source (not shown) provided on the signal line 21S. Similarly, a source follower circuit is configured by the MOS transistor 208Na and a constant current source (not shown) provided on the signal line 21N. The MOS transistor 208Sa and the row selection switch 208Sb configure a signal selection circuit portion 208S, and the MOS transistor 208Na and the row selection switch 208Nb configure a noise selection circuit portion 208N. A selection circuit portion 208 includes the signal selection circuit portion 208S and a noise selection circuit portion 208N.

The pixel 20 may have an addition switch 209S that adds the optical signals of an adjacent plurality of pixels 20. In an addition mode, the addition mode signal ADD becomes the active level and the addition switch 209S is turned on. Thus, the capacitors 207Sb of the adjacent pixels 20 are connected to each other by the addition switch 209S, and the optical signals are averaged. Similarly, the pixels 20 may have an addition switch 209N that adds the noise of the adjacent plurality of pixels 20. When the addition switch 209N is turned on, the capacitors 207Nb of the adjacent pixels 20 are connected to each other by the addition switch 209N to the noise are average. An addition portion 209 includes the addition switch 209S and the addition switch 209N.

The pixel 20 may also have a sensitivity changing portion 205 for changing the sensitivity. The pixel 20 may include, for example, a first sensitivity changing switch 205*a* and a second sensitivity changing switch 205'*a*, and their associated circuit elements. When the first changing signal WIDE becomes the active level, the first sensitivity changing switch 205*a* is turned on, and the capacity value of the first added capacity 205*b* is added to the capacity value of the charge-voltage conversion portion. This reduces the sensitivity of the pixel 20. When the second change signal WIDE2 becomes the active level, the second sensitivity change switch 205'*a* is turned on, and the capacity value of the second added capacity 205'*b* is added to the capacity value of the charge-voltage conversion portion. This further reduces the sensitivity of the pixel 20. By adding a function to reduce the sensitivity of the pixel 20 in this way, it becomes possible to receive a larger amount of light, thereby widening the dynamic range. When the first change signal WIDE becomes the active level, the enable signal ENw may be set to the active level to cause a MOS transistor 204'*a* to perform the source-follower operation instead of the MOS transistor 204*a*.

The radiation imaging apparatus 104 reads the output of the pixel circuit described above and converts it into a digital value (image information) by an analog-to-digital converter (not shown). The radiation imaging apparatus 104 transfers the image information converted into the digital value to the control apparatus 103. Thus, the obtaining unit 131 of the control apparatus 103 can obtain the image obtained by the radiation imaging.

Figure 3:
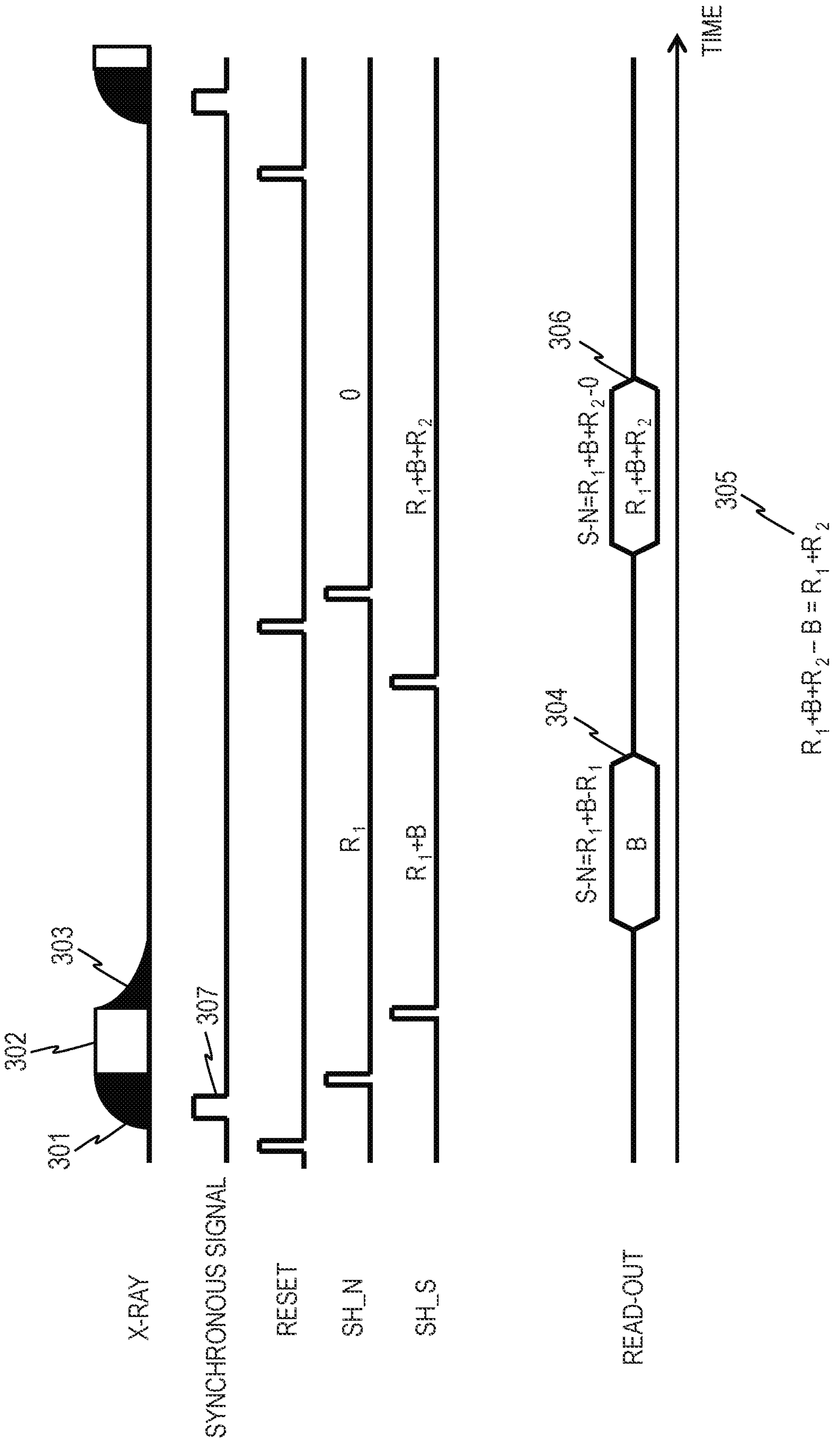
FIG. 3 is a timing chart for illustrating one example of a radiation imaging operation.
Figure 4:
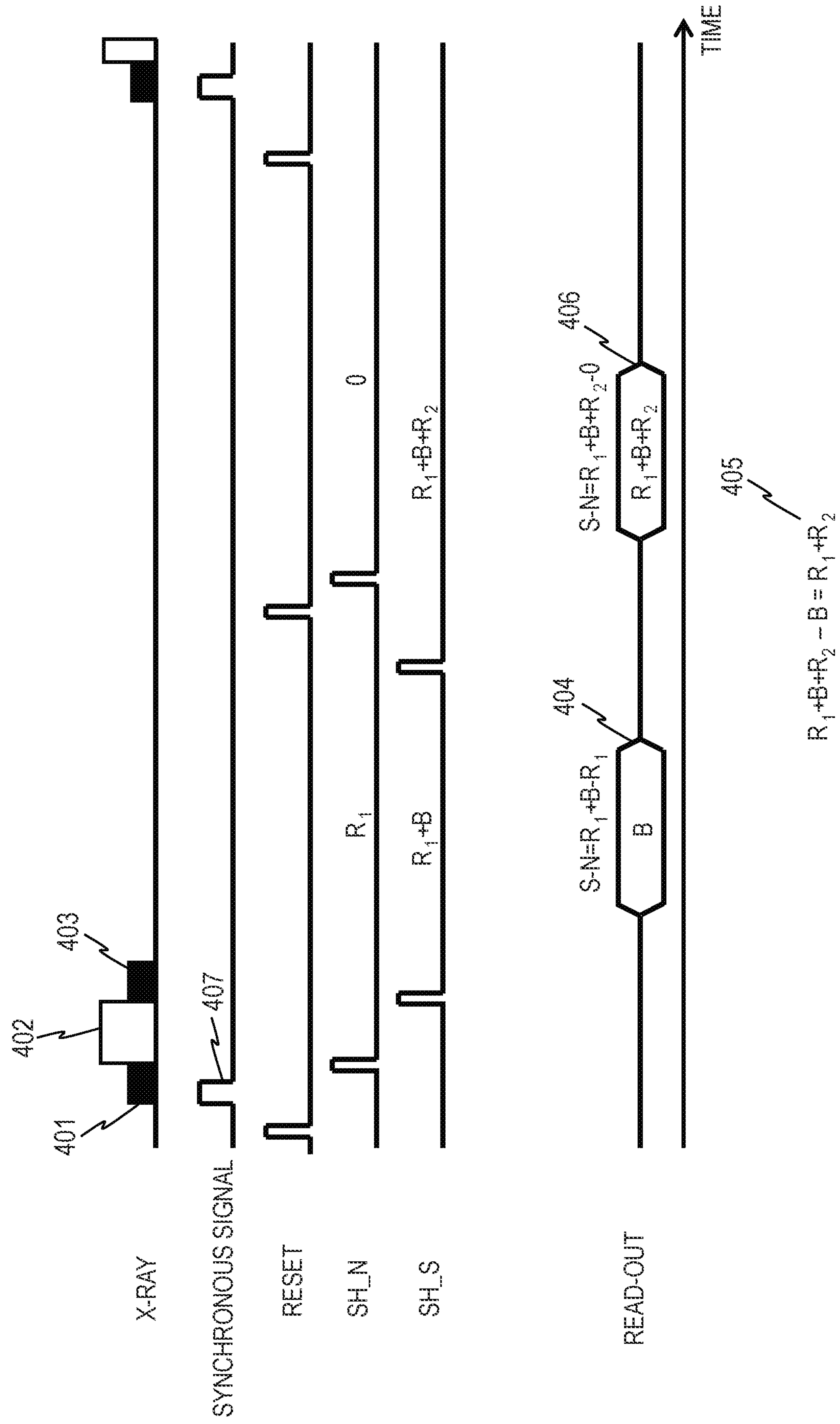
FIG. 4 is a timing chart for illustrating one example of the radiation imaging operation.

Next, with reference to FIG. 3 and FIG. 4, the radiation imaging operation of the radiation photographing system according to the first embodiment will be described. FIG. 3 and FIG. 4 are diagrams for illustrating examples of various driving timings in the imaging operation for performing the energy-subtraction processing in the radiation imaging system according to the first embodiment. FIG. 3 is a diagram for illustrating an example of the radiation imaging operation using a relatively inexpensive radiation tube of which the tube voltage (energy) cannot be switched. FIG. 4 is a diagram for illustrating an example of the radiation imaging operation using a radiation tube of which the tube voltage can be switched. The waveforms in the FIG. 3 and FIG. 4 show the timings of the X-ray exposure, synchronous signals, resetting of the photoelectric conversion element 201, driving of the sample-and-hold circuit portion 207, and readout of the image from the signal line 21, with the horizontal axis as the time. In FIG. 3 and FIG. 4, the waveforms in "X-RAY" show the tube voltage. Further, for the "X-RAY", black and white spots are provided, which are simply drawn to make it easier to distinguish the timing.

First, the example shown in FIG. 3 will be described. In this example, the photoelectric conversion element 201 is reset and then the X-ray is irradiated. The tube voltage of the X-ray is ideally a square wave, but the rise and the fall of the tube voltage take a finite time. In particular, in a case where the irradiation time is short for pulsed X-ray, the tube voltage is no longer considered to be a square wave, and the waveform is as shown in the "X-RAY" in FIG. 3. For this reason, the energies of the X-ray are different in the rising, stable, and falling phases of the X-ray.

In this regard, after the X-ray 301 in the rising phase is irradiated, sampling is performed by the noise sample-hold circuit 207N, and after the X-ray 302 in the stable phrase is irradiated, sampling is performed by the signal sample-hold circuit 207S. Then, the difference of the signal of the signal line 21N and the signal of the signal line 21S is read out as an image. At this time, the noise sample-hold circuit 207N holds the signal ($R_1$) of the X-ray 301 in the rising phrase, and the signal sample-hold circuit 207S holds the sum of the signal ($R_1$) of the X-ray 301 in the rising phrase and the signal (B) of the X-ray 302 in the stable phrase. Thus, an image 304 corresponding to the signal (B) of the X-ray 302 in the stable phase is read out as the difference of the signal of the signal line 21N and the signal of the signal line 21S.

Next, after the irradiation of the X-ray 303 in the falling phase and the readout of the image 304 are completed, the sampling is performed again by the signal sample-and-hold circuit 207S. Then, the photoelectric conversion element 201 is reset, the sampling is performed again by the noise sample-and-hold circuit 207N, and the difference of the signal of the signal line 21N and the signal of the signal line 21S are read out as an image. At this time, the noise sample-and-hold circuit 207N holds a signal in a state where no X-ray is irradiated. In addition, the signal sample-and-hold circuit 207S holds the sum of the signal ($R_1$) of the X-ray 301 in the rising phrase, the signal (B) of the X-ray 302 in the stable phrase, and the signal ($R_2$) of the X-ray 303 in the falling phrase. Therefore, an image 306 corresponding to the sum of the signal ($R_1$) of the X-ray 301 in the rising phrase, the signal (B) of the X-ray 302 in the stable phrase, and the signal ($R_2$) of the X-ray 303 in the falling phrase is read out as the difference of the signal of the signal line 21N and the signal of the signal line 21S. Then, by calculating the difference of the image 306 and the image 304, an image 305 corresponding to the sum of the signal ($R_1$) of the X-ray 301 in the rising phrase and the signal ($R_2$) of the X-ray 303 in the falling phrase is obtained.

The timing of resetting the sample-hold circuit portion 207 and the photoelectric conversion element 201 is determined by using the synchronous signal 307 that indicates the start of the X-ray irradiation from the radiation generating apparatus 101. As a method of detecting the start of the X-ray irradiation, a configuration in which the tube current of the radiation generating apparatus 101 is measured to determine whether the current value exceeds a preset threshold can be used. A configuration in which after the reset of the photoelectric conversion element 201 is completed, the signal of the pixel 20 is repeatedly read out to determine whether the pixel value exceeds a preset threshold can also be used. In addition, a configuration in which the radiation imaging apparatus 104 incorporates an X-ray detector different from the two-dimensional detector 106 and determines whether the measured value exceeds a preset threshold can be used. In any of the configurations, the sampling by the signal sample-and-hold circuit 207S, the sampling by the noise sample-and-hold circuit 207N, and the reset of the photoelectric conversion element 201 are performed after predetermined time elapses from the input of the synchronous signal 307.

Thus, the image 304 corresponding to the stable phase of the pulsed X-ray and the image 305 corresponding to the sum of the rising and falling phases of the pulsed X-ray can be obtained. Since the energies of the X-rays irradiated in the generation of the 2 images are different from each other, the energy-subtraction processing can be performed by performing a calculation between the 2 images.

Next, an example of the radiation imaging operation when a radiation tube of which the tube voltage can be switched is described with reference to FIG. 4. The example differs from the example shown in FIG. 3 in that the tube voltage of X-rays is actively switched.

In this example, the photoelectric conversion element 201 is first reset and then the X-ray 401 of a low-energy is irradiated. Then, after the sampling is performed by the noise sample-and-hold circuit 207N, the tube voltage is switched and the X-ray 402 of a high-energy is irradiated. After the X-ray 402 of the high-energy is irradiated, the sampling is performed by the signal sample-and-hold circuit 207S. Then, the tube voltage is switched and the irradiation of the X-ray 403 of the low-energy is performed. Further, the difference of the signal of signal line 21N and the signal of signal line 21S is read out as an image. At this time, the noise sample-hold circuit 207N holds the signal ($R_1$) of the X-ray 401 of the low-energy, and the signal sample-hold circuit 207S holds the sum of the signal ($R_1$) of the X-ray 401 of the low-energy and the signal (B) of the X-ray 402 of the high-energy. Therefore, the image 404 corresponding to the signal (B) of the X-ray 402 of high-energy is read out as the difference of the signal of the signal line 21N and the signal of the signal line 21S.

After the irradiation of the X-ray 403 of the low-energy and the readout of the image 404 are completed, the sampling is performed again by the signal sample-and-hold circuit 207S. Then, the photoelectric conversion element 201 is reset, the sampling is performed again by the noise sample-and-hold circuit 207N, and the difference of the signal of the signal line 21N and the signal of the signal line 21S are read out as an image. At this time, the noise sample-and-hold circuit 207N holds a signal in a state where no X-ray is irradiated. Further, the signal sample-and-hold circuit 207S holds the sum of the signal ($R_1$) of the X-ray 401 of the low-energy, the signal (B) of the X-ray 402 of the high-energy, and the signal ($R_2$) of the X-ray 403 of the low-energy. Therefore, an image 406 corresponding to the sum of the signal ($R_1$) of the X-ray 401 of the low-energy, the signal (B) of the X-ray 402 of the high-energy, and the signal ($R_2$) of the X-ray 403 of the low-energy is read out as the difference of the signal of signal line 21N and the signal of signal line 21S. Then, by calculating the difference of the image 406 and the image 404, an image 405 corresponding to the sum of the signal ($R_1$) of the X-ray 401 of the low-energy and the signal ($R_2$) of the X-ray 403 of the low-energy is obtained.

The synchronous signal 407 is the same as the synchronous signal 307 in the example shown in FIG. 3. By obtaining the image while actively switching the tube voltage in this way, the energy difference between the images of the low-energy and the high-energy can be made larger compared to the method described with reference to FIG. 3.

Next, the method of the energy-subtraction processing is described. The energy-subtraction processing in the first embodiment includes correction processing as pre-processing and image processing as post-processing in addition to the signal processing of the energy-subtraction processing.

Figure 5:
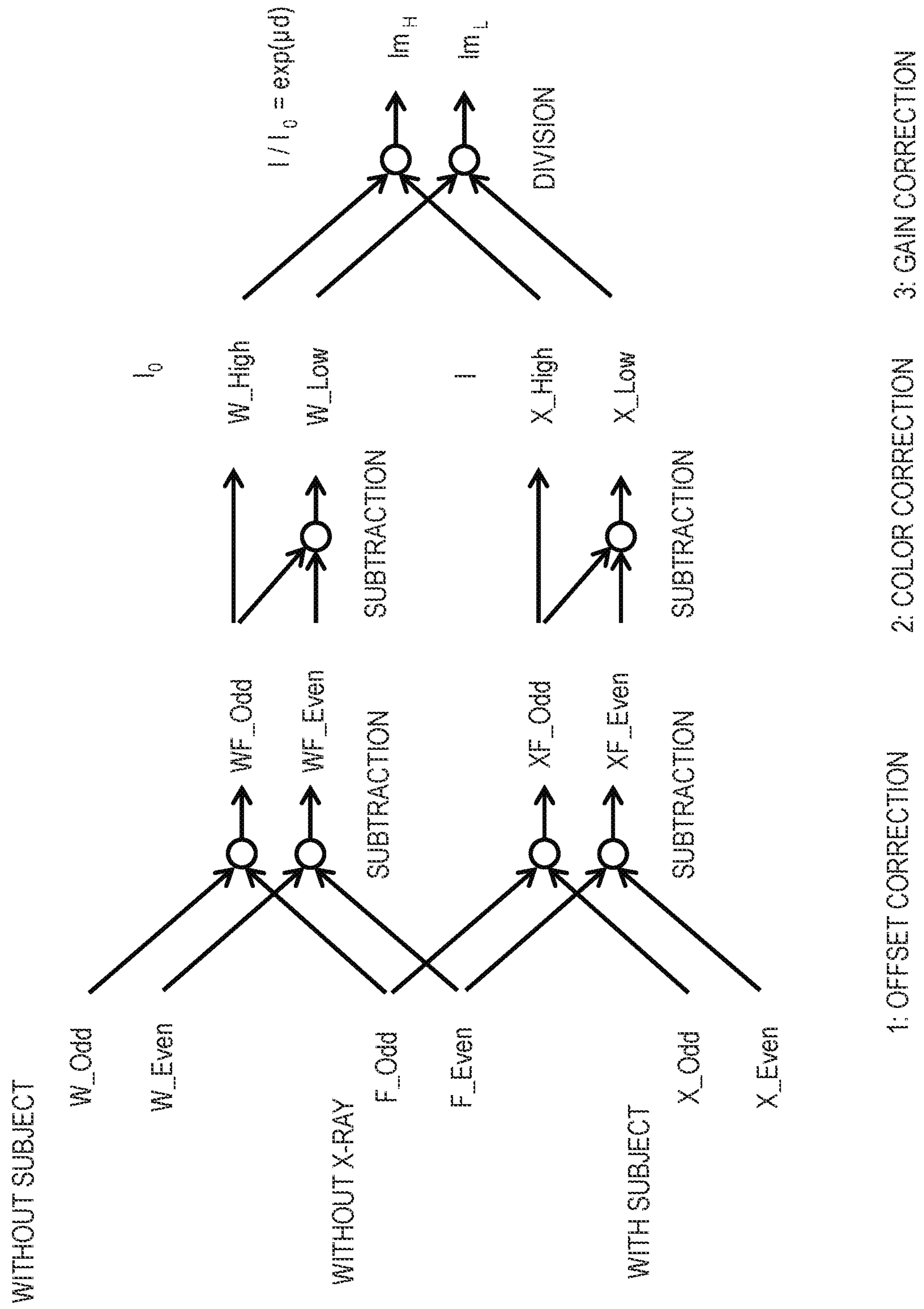
FIG. 5 is a block diagram of correction processing according to the first embodiment.

First, the correction processing as the pre-processing is described with reference to FIG. 5. FIG. 5 is a block diagram of the correction processing according to the first embodiment. Noted that in the first embodiment, an example in which a radiation photographing operation according to the example shown in FIG. 3 is performed is described.

First, the imaging is performed according to the drive shown in FIG. 3 without irradiating the X-ray to the radiation imaging apparatus 104, and the obtaining unit 131 obtains the captured image. At this time, two images corresponding to the image 304 and 306 are read out, and the first image (the image 304) is an image F_Odd and the second image (the image 306) is an image F_Even. The image F_Odd and the image F_Even are images corresponding to the fixed pattern noise (FPN) of the radiation imaging apparatus 104.

Next, the imaging is performed according to the drive shown in FIG. 3 by irradiating the X-ray to the radiation imaging apparatus 104 without the subject, and the obtaining unit 131 obtains the captured image. At this time, two images corresponding to the image 304 and 306 are read out, and the first image (the image 304) is an image W_Odd and the second image (the image 306) is an image W_Even. The image W_Odd and the image W_Even are images corresponding to the sum of the FPN of radiation imaging apparatus 104 and the signal according to the X-ray.

Therefore, by subtracting the image F_Odd from the image W_Odd and subtracting the image F_Even from the image W_Even, an image WF_Odd and an image WF_Even in which the FPN of the radiation imaging apparatus 104 is removed are obtained. In the first embodiment, such correction processing is called offset correction.

The image WF_Odd is an image corresponding to the X-ray 302 in the stable phase, and the image WF_Even is an image corresponding to the sum of the X-ray 301 in the rising phase, the X-ray 302 in the stable phase, and the X-ray 303 in the falling phase. Therefore, by subtracting the image WF_Odd from the image WF_Even, an image corresponding to the sum of the X-ray 301 in the rising phase and the X-ray 303 in the falling phase is obtained. The energies of the X-ray 301 in the rising phase and the X-ray 303 in the falling phase are lower than the energy of the X-ray 302 in the stable phase. Therefore, by subtracting the image WF_Odd from the image WF_Even, a low-energy image W_Low in a state where the subject is absent is obtained. Also, a high-energy image WF_High in a state where the subject is absent is obtained from the image W_Odd. In the first embodiment, such correction processing is called color correction.

Next, the imaging is performed according to the drive shown in FIG. 3 by irradiating the X-ray to the radiation imaging apparatus 104 in a state where the subject exists, and the obtaining unit 131 obtains the captured image. At this time, two images corresponding to the image 304 and 306 are read out, and the first image (the image 304) is an image X_Odd and the second image (the image 306) is an image X_Even. The generating unit 132 can obtain a low-energy image X_Low in the state where the subject exists and a high-energy image X_High in the state where the subject exists by performing offset correction and color correction on these images in the same manner as the offset correction and the color correction in the state where the subject is absent.

Here, the thickness of subject is represented as d, the linear attenuation coefficient of the subject is represented as μ, the output of the pixel 20 in the state where the subject is absent is represented as $I_0$, and the output of the pixel 20 in the state where the subject exists is represented as I, the following equation (1) is satisfied.

$$I = I_0 \exp(-\mu d) \tag{1}$$

Here, by modifying the equation (1), the following equation (2) is obtained.

$$\frac{I}{I_0} = \exp(-\mu d) \tag{2}$$

The right side of equation (2) indicates the attenuation ratio of the subject. The attenuation ratio of the subject is a real number between 0-1.

Therefore, by dividing the low-energy image X_Low in the state where the subject exists by the low-energy image W_Low in the state where the subject is absent, an image of the attenuation ratio in the low-energy (a low-energy image $Im_L$) is obtained. Similarly, by dividing the high-energy image X_High in the state where the subject exists by the high-energy image W_High in the state where the subject is absent, an image of the attenuation ratio in the high-energy (a high-energy image $Im_H$) is obtained. In the first embodiment, such correction processing is called gain correction. In the first embodiment, the generating unit 132 can generate and obtain the low-energy image $Im_L$ and the high-energy image $Im_H$ by performing the correction processing including the offset correction, the color correction and the gain correction as described above.

Figure 6:
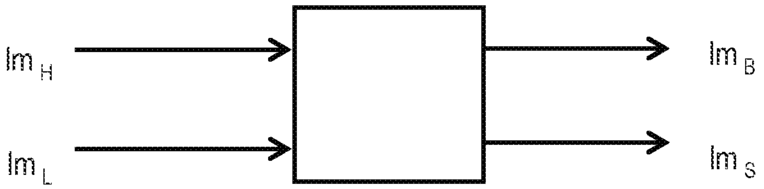
FIG. 6 is a block diagram of signal processing of energy-subtraction processing.

Next, before describing the energy-subtraction processing using the image-quality improving model according to the first embodiment, signal processing of the energy-subtraction processing will be described with reference to FIG. 6. FIG. 6 is a block diagram of the signal processing in the energy-subtraction processing. In the signal processing of the energy-subtraction processing, an image of the thickness of bone (a bone image $Im_B$) and an image of the thickness of soft tissue (a soft tissue image $Im_S$) are obtained from the low-energy image $Im_L$ and the high-energy image $Im_H$ obtained by the correction processing described with reference to FIG. 5.

The energy of X-ray photons is represented as E, the number of photons for the energy E is represented as N(E), the thickness of the bone is represented as B, and the thickness of the soft tissue is represented as S. Further, the linear attenuation coefficient of the bone for the energy E is represented as $\mu_B(E)$, the linear attenuation coefficient of the soft tissue for the energy E is represented as $\mu_S(E)$, and the attenuation ratio is represented as $I/I_0$. In this case, the following equation (3) is satisfied.

$$\frac{I}{I_0} = \frac{\int_0^\infty N(E)\exp\{-\mu_B(E)B - \mu_S(E)S\}E dE}{\int_0^\infty N(E)E dE} \tag{3}$$

The number of the photon N(E) for the energy E is the spectrum of the X-rays. The spectrum of the X-rays is obtained by simulation or measurement. Further, the linear attenuation coefficient $\mu_B(E)$ of the bone for the energy E and the linear attenuation coefficient $\mu_S(E)$ of the soft tissue for the energy E are obtained from databases of NIST (National Institute of Standards and Technology), etc. Therefore, using the equation (3), it is possible to calculate the attenuation ratio $I/I_0$ for any bone thickness B, soft tissue thickness S, and X-ray spectrum N(E).

Here, the spectrum of the X-rays of the low-energy is represented as $N_L(E)$ and the spectrum of the X-rays of the high-energy is represented as $N_H(E)$. In this case, the following equation (4) is satisfied.

$$L = \frac{\int_0^\infty N_L(E)\exp\{-\mu_B(E)B - \mu_S(E)S\}EdE}{\int_0^\infty N_L(E)EdE} \tag{4}$$

$$H = \frac{\int_0^\infty N_H(E)\exp\{-\mu_B(E)B - \mu_S(E)S\}EdE}{\int_0^\infty N_H(E)EdE}$$

By solving the nonlinear simultaneous equations in the equation (4), the bone thickness B and the soft tissue thickness S can be obtained.

Here, a case where the Newton Raphson method as a kind of iterative solution is used as a representative method for solving the nonlinear simultaneous equations is described. First, when the number of iterations of the Newton Raphson method is represented as m, the bone thickness after the m-th iteration is represented as $B^m$, and the soft tissue thickness after the m-th iteration is represented as $S^m$, the attenuation ratio $H^m$ of the high-energy after the m-th iteration and the attenuation ratio $L^m$ of the low-energy after the m-th iteration are represented by the following equation (5).

$$L^m = \frac{\int_0^\infty N_L(E)\exp\{-\mu_B(E)B^m - \mu_S(E)S^m\}EdE}{\int_0^\infty N_L(E)EdE} \tag{5}$$

$$H^m = \frac{\int_0^\infty N_H(E)\exp\{-\mu_B(E)B^m - \mu_S(E)S^m\}EdE}{\int_0^\infty N_H(E)EdE}$$

Further, the change ratio of the attenuation ratio when the thickness minutely changes is represented by the following equation (6):

$$\frac{\partial H^m}{\partial B^m} = \frac{\int_0^\infty -\mu_B(E)N_H(E)\exp\{-\mu_B(E)B^m - \mu_S(E)S^m\}EdE}{\int_0^\infty N_H(E)EdE} \tag{6}$$

$$\frac{\partial L^m}{\partial B^m} = \frac{\int_0^\infty -\mu_B(E)N_L(E)\exp\{-\mu_B(E)B^m - \mu_S(E)S^m\}EdE}{\int_0^\infty N_L(E)EdE}$$

$$\frac{\partial H^m}{\partial S^m} = \frac{\int_0^\infty -\mu_S(E)N_H(E)\exp\{-\mu_B(E)B^m - \mu_S(E)S^m\}EdE}{\int_0^\infty N_H(E)EdE}$$

-continued $$\frac{\partial L^m}{\partial S^m} = \frac{\int_0^\infty -\mu_S(E)N_L(E)\exp\{-\mu_B(E)B^m - \mu_S(E)S^m\}EdE}{\int_0^\infty N_L(E)EdE}$$

In this case, the bone thickness $B^{m+1}$ and the soft tissue thickness $S^{m+1}$ after the m+1-th iteration are represented by the following equation (7) using the attenuation ratio H of the high-energy and the attenuation ratio L of the low-energy.

$$\begin{bmatrix} B^{m+1} \\ S^{m+1} \end{bmatrix} = \begin{bmatrix} B^m \\ S^m \end{bmatrix} + \begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} \begin{bmatrix} H - H^m \\ L - L^m \end{bmatrix} \tag{7}$$

Here, the inverse matrix of the 2×2 matrix is expressed by the following equation from the Cramer's rule when the determinant of the 2×2 matrix is represented as det.

$$\det = \frac{\partial H^m}{\partial B^m}\frac{\partial L^m}{\partial S^m} - \frac{\partial H^m}{\partial S^m}\frac{\partial L^m}{\partial B^m} \tag{8}$$

$$\begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} = \frac{1}{\det}\begin{bmatrix} \frac{\partial L^m}{\partial S^m} & -\frac{\partial H^m}{\partial S^m} \\ -\frac{\partial L^m}{\partial B^m} & \frac{\partial H^m}{\partial B^m} \end{bmatrix}$$

Therefore, by substituting equation (8) into equation (7), the following equation (9) is obtained.

$$B^{m+1} = B^m + \frac{1}{\det}\frac{\partial L^m}{\partial S^m}(H - H^m) - \frac{1}{\det}\frac{\partial H^m}{\partial S^m}(L - L^m) \tag{9}$$

$$S^{m+1} = S^m + \frac{1}{\det}\frac{\partial L^m}{\partial B^m}(H - H^m) - \frac{1}{\det}\frac{\partial H^m}{\partial B^m}(L - L^m)$$

By repeating such calculations, the difference between the attenuation ratio $H^m$ of the high-energy after the m-th iteration and the measured attenuation ratio H of the high-energy infinitely approaches 0. The same is true for the attenuation rate L of the low-energy. Therefore, the bone thickness $B^m$ after the m-th iteration converges to the bone thickness B, and the soft tissue thickness $S^m$ after the m-th iteration converges to the soft tissue thickness S. In this way, the nonlinear simultaneous equations of the equation (4) can be solved. Therefore, by calculating equation (4) for all pixels, the bone image $Im_B$ and the soft tissue image $Im_S$ can be obtained from the low-energy image $Im_L$ and the high-energy image $Im_H$.

Note that, to simplify the explanation, the bone thickness B and the soft tissue thickness S are calculated by the energy-subtraction processing, but the first embodiment is not limited to such a form. For example, water thickness and contrast medium thickness may be calculated by the energy-subtraction processing. In this case, the linear attenuation coefficient of the water for energy E and the linear attenuation coefficient of the contrast medium for the energy E may also be obtained from databases of NIST, etc. According to the energy-subtraction processing, the thicknesses of any two kinds of materials can be calculated.

In the above description, the nonlinear simultaneous equations are solved using the Newton-Raphson method. However, the method of solving the nonlinear simultaneous equations is not limited to this form. For example, an iterative solution method such as the least-squares method or the bisection method may be used. Further, a method of calculating the bone thickness B and the soft tissue thickness S is not limited to this form in which the nonlinear simultaneous equations are solved by the iterative method. For example, a table may be generated by obtaining the bone thicknesses B and the soft tissue thicknesses S for various combinations of the attenuation ratios H of the high-energy and the attenuation ratios L of the low-energy in advance, and the bone thickness B and the soft tissue thickness S may be obtained at high speed by referring to the table.

In the above description, a method for generating the bone image $Im_B$ and the soft tissue image $Im_S$ by performing the energy-subtraction processing on the high-energy image $Im_H$ and the low-energy image $Im_L$ is described. On the other hand, the energy-subtraction processing using an image-quality improving model, which is a learned model for outputting a high image-quality image (an image with high image-quality), according to the first embodiment will be described below. In the first embodiment, the processing unit 133 generates the high image-quality energy-subtraction images (the bone image $Im_B$ and the soft tissue image $Im_S$) with a reduced noise based on the high-energy image $Im_H$ and the low-energy image $Im_L$ by using the image-quality improving model.

(Image-Quality Improving Model)

Figure 7:
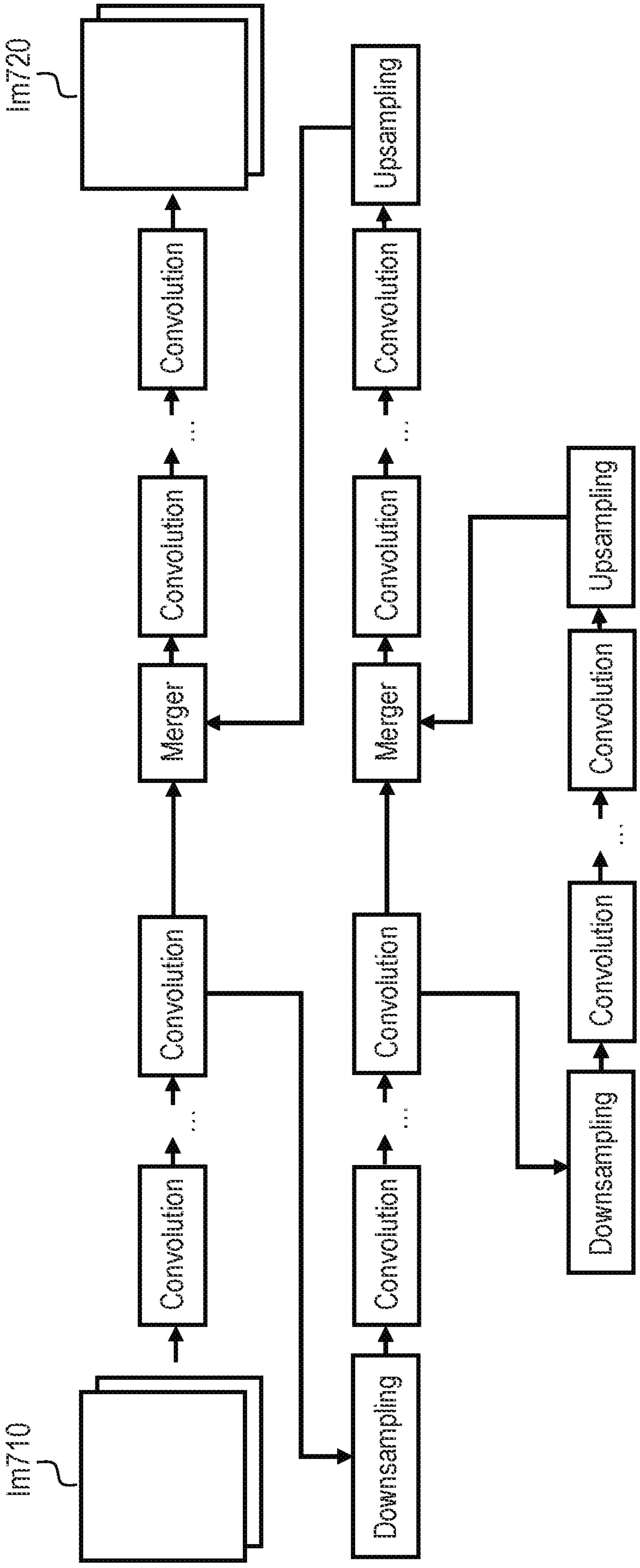
FIG. 7 is a diagram for illustrating an example of a configuration of a neural network relating to an image-quality improving model.

Hereafter, the image-quality improving model according to the first embodiment will be described with reference to FIG. 7. In the first embodiment, the image-quality improving model is stored in the storage 135 and used by the processing unit 133 for processing, but the image-quality improving model may be included in an external apparatus (not shown) connected to the controlling apparatus 103.

The image-quality improving model according to the first embodiment is a learned model obtained by training (learning) according to the machine learning algorithm. In the first embodiment, training data comprising pairs of input data including a low image-quality image having a specific imaging-condition, which is assumed as a processing target, and output data including a high image-quality image corresponding to the input data is used for the training of the machine learning model according to the machine learning algorithm. Specifically, the specific imaging-condition includes a predetermined imaging site, a predetermined imaging method, a predetermined tube voltage of the X-ray, a predetermined image size, etc.

Here, a general learned model is described briefly. A learned model is a machine learning model that has performed training (learning) with respect to any machine learning algorithm using appropriate training data in advance. The training data includes pairs of one or more input data and output data (ground truth). The format and the combination of the input data and the output data of the pairs included in the training data may be suitable for a desired configuration. For example, the both of the pair may be images, one of the pair may be an image and the other may be a numerical value, the one of the pair may include a plurality of images and the other may be a character string.

Specifically, the training data includes, for example, training data (hereinafter, referred to as "first training data") which comprises pairs of a low image-quality image with much noises obtained by normal imaging and a high image-quality image captured with a high dose, and so on, can be mentioned. Another example of the training data includes training data (hereinafter, referred to as "second training data"), which comprises pairs of an image obtained by the radiation imaging apparatus 104 and an imaging site label corresponding to the image. The imaging site label may be a unique numerical value or a character string indicating a site.

At this time, if input data is input to the learned model, output data according to the design of the relevant learned model is output. The learned model, for example, outputs the output data which has high probability of corresponding to the input data, according to the tendency for which the learned model was trained using the training data. The learned model, for example, can also output likelihood (reliability, or probability) of corresponding to the input data as a numerical value for each of kind of the output data, according to the tendency for which the learned model was trained using the training data.

Specifically, for example, if a low image-quality image with much noises obtained by the normal imaging is input to the machine learning model that has performed training using the first training data, the machine learning model outputs a high image-quality image corresponding to an image captured with a high dose. Also, for example, if an image obtained by imaging is input to a machine learning model which has performed training using the second training data, the machine learning model outputs an imaging site label of the imaging site imaged in the corresponding image, or outputs probability for each imaging site label. Note that with respect to the machine learning model, from the viewpoint of quality maintenance, the machine learning model can be configured so that the output data output by itself is not used as training data.

Further, machine learning algorithms include techniques relating to deep learning such as a convolutional neural network (CNN). In a technique relating to deep learning, if the settings of parameters with respect to a layer group and a node group constituting a neural network differ, in some cases the degrees to which a tendency trained using training data is reproducible in the output data will differ. For example, in a machine learning model of deep learning that uses the first training data, if more appropriate parameters are set, in some cases an image with higher image-quality can be output. Further, for example, in a machine learning model of deep learning that uses the second training data, if more appropriate parameters are set, the probability of outputting a correct imaging site label may become higher.

Specifically, the parameters in the case of a CNN can include, for example, the kernel size of the filters, the number of filters, the value of a stride, and the dilation value which are set with respect to the convolutional layers, and also the number of nodes output from a fully connected layer. Note that, the parameter group and the number of training epochs can be set to values preferable for the utilization form of the learned model based on the training data. For example, based on the training data, a parameter group or a number of epochs can be set that enables the output of an image with higher image quality or the output of a correct imaged site label with a higher probability.

One method for determining such a parameter group or the number of epochs will now be described as an example. First, 70% of the pairs included in the training data is set for training use, and the remaining 30% is set at random for evaluation use. Next, training of the machine learning model is performed using the pairs for training use, and at the end of each training epoch, a training evaluation value is calculated using the pairs for evaluation use. The term "training evaluation value" refers to, for example, an average value of a group of values obtained by evaluating, by a loss function, the output when input data included in each pair is input to the machine learning model that is being trained, and the output data that corresponds to the input data. Finally, the parameter group and the number of epochs when the training evaluation value is smallest are determined as the parameter group and the number of epochs of the relevant machine learning model. Note that, by dividing pairs included in the training data into pairs for training use and pairs for evaluation use and determining the number of epochs in this way, the occurrence of a situation in which the machine learning model overlearns with respect to the pairs for training can be prevented.

Here, the image-quality improving model according to the first embodiment is configured as a module that outputs a high image-quality energy-subtraction image based on the input low image-quality energy image. Here, the term "improving image-quality" as used in the description refers to generate an image with image quality that is more suitable for image examination from the input image, and the term "high image-quality" refers to an image of which image quality is more suitable for image examination. Further, the term "low quality-image" refers to an image obtained by imaging without setting any particular settings in order to obtain high image-quality such as, for example, a two-dimensional image or a three-dimensional image obtained by X-ray imaging, CT, etc., or a three-dimensional moving image of CT which is obtained by continuous imaging, etc. Specifically, the low image-quality image includes, for example, an image captured with a low dose by X-ray imaging apparatus or CT, etc.

Further, if a high image-quality image with little noise or high contrast is used for various analysis processing and image analysis such as region segmentation processing of a CT image or the like, in many cases analysis can be performed more accurately than a case in which low quality image is used. Therefore, the high image-quality image output by the high image-quality model may be useful for not only the image examination but also the image analysis.

Furthermore, the content of image quality suitable for image examination depends on what it is desired to examine in various image examination. Therefore, while it is not possible to say so unconditionally, for example, image-quality suitable for image examination includes image-quality in which the amount of noise is low, the contrast is high, the imaging target is displayed in colors and gradations which make the imaging target easy to observe, the image size is large, and the resolution is high. In addition, image-quality suitable for image examination can include image-quality such that objects or gradations which do not actually exist that were rendered during the process of image generation are removed from the image.

In the image processing technique that constitutes the energy-subtraction processing performed by the processing unit 133 in the first embodiment, processing which uses various machine learning algorithms such as deep learning is performed. Note that, in the image processing techniques, in addition to processing using the machine learning algorithms, any existing processing such as various kinds of image filtering processing, matching processing using a database of high image-quality images corresponding to similar images, and knowledge-based image processing may be performed.

A configuration example of the CNN relating to the image-quality improving model according to the first embodiment will be described below with reference to FIG. 7. FIG. 7 is a diagram for illustrating an example of a configuration of the image-quality improving model. The configuration shown in FIG. 7 includes a plurality of layers that are responsible for the processing of processing and outputting input values. As the kinds of the layers included in the configuration, there are a convolution layer, a downsampling layer, an upsampling layer, and a merging (Merger) layer, as shown in FIG. 7.

The convolutional layer is a layer that performs the convolutional processing on input values according to parameters, such as the kernel size of a set filter, the number of filters, the value of a stride, and the value of dilation. Note that the number of dimensions of the kernel size of a filter may also be changed according to the number of dimensions of an input image.

The downsampling layer is a layer that performs the processing of making the number of output values less than the number of input values by thinning or combining the input values. Specifically, for example, there is Max Pooling processing as such processing.

The upsampling layer is a layer that performs the processing of making the number of output values more than the number of input values by duplicating the input values or adding a value interpolated from the input values. Specifically, for example, there is linear interpolation processing as such processing.

The merging layer is a layer to which values, such as the output values of a certain layer and the pixel values constituting an image, are input from a plurality of sources, and that combines them by concatenating or adding them.

In such a configuration, values obtained by outputting values constituting an input image Im710 via a convolution processing block, and the pixel values constituting the input image Im710 are combined in the merging layer. Then, a high image-quality image Im720 is generated using the combined pixel values in the last convolution layer.

Note that caution is required, since when the setting of the parameters to the layers and nodes constituting a neural network is different, the degree with respect to tendency trained from the training data, that can be reproduced at the inference may be different. In other words, in many cases, since appropriate parameters are different depending on the mode at the time of implementation, the parameters can be changed to preferable values according to the needs.

Additionally, the CNN may obtain better characteristics not only by changing the parameters as described above, but also by changing the configuration of the CNN. The better characteristics are, for example, a high accuracy of the noise reduction on a radiation image which is output, a short time for processing, and a short time taken for training of a machine learning model.

Note that the configuration of the CNN used in the present embodiment is a U-net type machine learning model that includes the function of an encoder including a plurality of hierarchies including a plurality of downsampling layers, and the function of a decoder including a plurality of hierarchies including a plurality of upsampling layers. In other words, the configuration of the CNN includes a U-shaped configuration that has an encoder function and a decoder function. The U-net type machine learning model is configured (for example, by using a skip connection) such that the geometry information (space information) that is made ambiguous in the plurality of hierarchies configured as the encoder can be used in a hierarchy of the same dimension (mutually corresponding hierarchy) in the plurality of hierarchies configured as the decoder.

Although not illustrated, as an example of change of the configuration of the CNN, for example, a batch normalization (Batch Normalization) layer, and an activation layer using a normalized linear function (Rectifier Linear Unit) may be incorporated after the convolutional layer.

Here, a GPU can perform efficient arithmetic operations by performing parallel processing of larger amounts of data. Therefore, in a case where training is performed a plurality of time using a machine learning algorithm such as deep learning, it is effective to perform the processing with a GPU. Thus, in the first embodiment, a GPU is used in addition to the CPU for processing performed by the processing unit 133, which functions as an example of a training unit. Specifically, when a training program including a learning model is executed, the training is performed by the CPU and the GPU cooperating to perform arithmetic operations. Note that, with respect to the processing of the training unit, the arithmetic operations may be performed only by the CPU or the GPU. Further, the energy-subtraction processing according to the first embodiment may also be performed by using the GPU, similarly to the training unit. If the learned model is provided in an external apparatus, the processing unit 133 need not function as a training unit.

The learning unit may also include an error detecting unit and an updating unit (not illustrated). The error detecting unit obtains an error between output data output from the output layer of the neural network according to input data input to the input layer, and the ground truth. The error detecting unit may calculate the error between the output data from the neural network and the ground truth using a loss function. Further, based on the error obtained by the error detecting unit, the updating unit updates combining weighting factors between nodes of the neural network or the like so that the error becomes small. The updating unit updates the combining weighting factors or the like using, for example, the error back-propagation method. The error back-propagation method is a method that adjusts combining weighting factors between the nodes of each neural network or the like so that the above error becomes small.

Note that, when using some image processing techniques such as image processing using a CNN, it is necessary to pay attention to the image size. Specifically, it should be kept in mind that, to overcome a problem such as the image-quality of a peripheral part of a high image-quality image not being sufficiently improved, in some cases different image sizes are required for a low image-quality image that is input and a high image-quality image that is output.

Although it is not specifically described in the first embodiments in order to provide a clear description, in a case where an image-quality improving model is adopted that requires different image sizes for an image that is input to the image-quality improving model and an image that is output therefrom, it is assumed that the image sizes are adjusted in an appropriate manner. Specifically, padding is performed with respect to an input image such as an image that is used in training data for training a machine learning model or an image to be input to an image-quality improving model, or imaging regions at the periphery of the relevant input image are joined together to thereby adjust the image size. Note that, a region which is subjected to padding is filled using a fixed pixel value, or is filled using a neighboring pixel value, or is mirror-padded, in accordance with the characteristics of the image-quality improving technique so that image-quality improving can be effectively performed.

Further, an image-quality improving processing in the processing unit 133 may be performed using only one image processing technique, and be performed using a combination of two or more image processing techniques. In addition, processing of a group of a plurality of image-quality improving techniques may be performed in parallel to generate a plurality of high image-quality images, and a high image-quality image with the highest image-quality may be then finally selected as the high image-quality image. Note that, the selection of the high image-quality image with the highest image-quality may be automatically performed using image-quality evaluation indexes, or may be performed by displaying the plurality of high image-quality images on a user interface (UI) provided in the display unit 120 or the like so that selection may be performed according to an instruction of the examiner (operator).

Note that, since there are also cases where an image that has not been subjected to image-quality improvement is suitable for image examination, an energy-subtraction image that has not been subject to image-quality improvement may be added to the objects for selection of the final image. Further, parameters may be input into the image-quality improving model together with the low image-quality image. For example, a parameter specifying the degree to which to perform image-quality improving, or a parameter specifying an image filter size to be used in an image processing technique may be input to the image-quality improving model together with the input image.

(Training Data of Image-Quality Improving Model)

Next, training data of the image-quality improving model according to the first embodiment will be described. The input data of the training data according to the first embodiment is a low image-quality energy image that is obtained by using the same model of equipment as the radiation imaging apparatus 104 and the same settings as the radiation imaging apparatus 104. Further, the ground truth of the training data of the image-quality improving model is a high image-quality energy-subtraction image that is obtained by using settings related to imaging-condition with a high dose or image processing, such as, averaging processing. Specifically, the output data may include, for example, a high image-quality energy-subtraction image obtained by performing the image processing such as the averaging processing on an energy-subtraction image (source image) group obtained by performing the imaging a plurality of times. Further, the ground truth of the training data may be, for example, a high image-quality energy-subtraction image calculated from a high image-quality energy image obtained by the imaging with a high dose. Furthermore, the ground truth of the training data may be, for example, a high image-quality energy-subtraction image calculated from a high image-quality energy image that is obtained by performing averaging processing on an energy image group obtained by performing the imaging a plurality of times.

By using the image-quality improving model that has been trained in this way, the processing unit 133 can output a high image-quality energy-subtraction image in which noise reduction and the like are performed by the averaging processing and the like when an energy image obtained by low dose imaging is input. Therefore, the processing unit 133 can generate a high image-quality energy-subtraction image suitable for image examination based on low image-quality image, which is an input image.

The example of using averaged image as the output data of the training data is described. However, the output data of the training data of the image-quality improving model is not limited to this example. The ground truth of the training data may be a high image-quality image corresponding to the input data. Therefore, the ground truth of the training data may be, for example, an image which has been subjected to contrast correction suitable for examination, an image of which the resolution has been improved, etc.

Further, an energy-subtraction image obtained from an image obtained by performing image processing using statistical processing such as maximum a posteriori probability estimation (MAP estimation) processing on a low image-quality energy image as the input data may be used as the output data of the training data. Furthermore, an image that is obtained by performing the image processing such as the MAP estimation processing on an energy-subtraction image generated from a low image-quality energy image may be used as the output data of the training data. Any known method may be used for generating the high image-quality image.

In addition, a plurality of image-quality improving models independently performing various image-quality improving processing such as noise reduction, contrast adjustment, and resolution improvement may be prepared as the image quality improving model. Further, one image-quality improving model performing at least two image-quality improving processing may be prepared. In these cases, a high image-quality energy-subtraction image corresponding to the desired processing may be used as the output data of the training data. For example, for an image-quality improving model that includes individual processing such as noise reduction processing, a high image-quality energy-subtraction image that has be subjected to the individual processing such as the noise reduction processing may be used as the output data of the training data. For an image-quality improving model for performing a plurality of image-quality improving processing, for example, a high image-quality energy-subtraction image that has been subjected to noise reduction processing and contrast correction processing may be used as the output data of the training data.

Figure 8A:
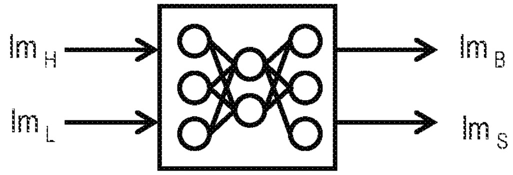
FIG. 8A is a block diagram for illustrating an example of generation processing of energy-subtraction images according to the first embodiment.

The training data of the image-quality improving model used by the processing unit 133 according to the first embodiment will be described more specifically below with reference to FIG. 8A. In the first embodiment, as shown in FIG. 8A, high-energy image $Im_H$ and low-energy image $Im_L$ captured with a low dose are used as the input data of the training data. A high image-quality bone image $Im_B$ and a high image-quality soft tissue image $Im_S$ obtained from a high image-quality high-energy image and a high image-quality low-energy image captured with a high dose are used as the output data of the training data. The high-image-quality bone image $Im_B$ and the high-image-quality soft tissue image $Im_S$ obtained by performing the averaging processing or the statistical processing such as the MAP estimation processing on a plurality of high-energy images $Im_H$ and a plurality of low-energy images $Im_L$ may be used as the output data of the training data.

By using such training data, a learned model corresponding to the combination of the input data (the high-energy image $Im_H$ and the low-energy image $Im_L$) according to the tube voltage can be easily constructed while reducing the load of imaging. Further, by constructing the learned model in this way, many nonlinear calculation processing included in the energy-subtraction processing can be included in the inference by the machine learning algorithm such as deep learning.

The image-quality improving model according to the first embodiment can have two input channels and two output channels corresponding to the input data and the output data. However, the number of channels of the input data and the output data of the image-quality improving model may be set appropriately.

Moreover, the processing unit 133 according to the first embodiment can apply image processing as a post-processing to the high image-quality bone image $Im_B$ and the high image-quality soft tissue image $Im_S$ output from the image-quality improving model. Here, the image processing in the first embodiment may be processing for performing any calculations on the energy-subtraction image. The processing unit 133 may perform adjustment processing such as contrast adjustment and gradation adjustment as the image processing for the high image-quality bone image $Im_B$ and the high image-quality soft tissue image $Im_S$. Further, the processing unit 133 may apply a time-directional filter such as a recursive filter or a spatial-directional filter such as a Gaussian filter to the bone image $Im_B$ and the soft tissue image $Im_S$, as the image processing. Furthermore, the processing unit 133 may generate a virtual monochromatic image described later from the high image-quality bone image $Im_B$ and the high image-quality soft tissue image $Im_S$ as the image processing.

The processing unit 133 may also generate DSA (Digital Subtraction Angiography) images of the bone and the soft tissue using the high image-quality bone image $Im_B$ and the high image-quality soft tissue image $Im_S$ as the image processing. In this case, the processing unit 133 obtains, by using the image-quality improving model, a mask image $Im_{BM}$ of the bone thickness and a mask image $Im_{SM}$ of the soft tissue thickness from a low-energy image $Im_L$ M and a high-energy image $Im_H$ M captured before injecting a contrast medium. Further, the processing unit 133 obtains, by using the image-quality improving model, a live image $Im_{BL}$ of the bone thickness and a live image $Im_{SL}$ of the soft tissue thickness from a low-energy image $Im_{LL}$ and a high-energy image $Im_{HL}$ captured after injecting the contrast medium. The processing unit 133 can then generate a DSA image of the bone by subtracting the mask image $Im_{BM}$ of the bone thickness from the live image $Im_{BL}$ of the bone thickness and a DSA image of the soft tissue by subtracting the mask image $Im_{SM}$ of the soft tissue thickness from the live image $Im_{SL}$ of the soft tissue thickness.

Note that images to be finally displayed that is obtained by performing post-processing such as contrast correction on the high image-quality bone image $Im_B$ and the high image-quality soft tissue image $Im_S$ may be used as the output data of the training data.

Further, the processing unit 133 may generate an analysis value by performing any analysis processing on the high image-quality bone image $Im_B$ and the high image-quality soft tissue image $Im_S$ output from the image-quality improving model. For example, the processing unit 133 may calculate an analysis value such as bone density using the high image-quality bone image $Im_B$ and the high image-quality soft tissue image $Im_S$. Any known method may be used for the analysis of bone density and the like.

(Other Examples of Image-Quality Improving Model)

Note that the input data and the output data of the image-quality improving model are not limited to the above-mentioned combinations. The image-quality improving model according to the first embodiment may be any image-quality improving model which is used by the processing unit 133 for generating a high image-quality bone image $Im_B$ and a high image-quality soft tissue image $Im_S$ based on a high-energy image $Im_H$ and a low-energy image $Im_L$. In this regard, other examples of the image-quality improving model will be described with reference to FIG. 8B to FIG. 8D.

Figure 8B:
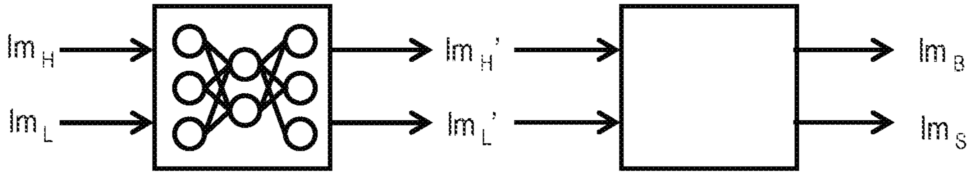
FIG. 8B is a block diagram for illustrating an example of the generation processing of the energy-subtraction images according to the first embodiment.
Figure 8C:
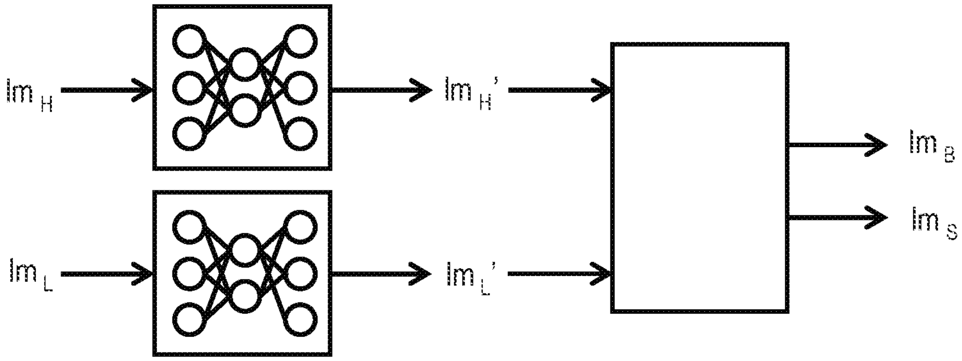
FIG. 8C is a block diagram for illustrating an example of the generation processing of the energy-subtraction images according to the first embodiment.

For example, a learned model for inferring a high image-quality energy image from a low image-quality energy image as shown in FIG. 8B and FIG. 8C may be constructed as the image-quality improving model. FIG. 8B is a diagram for illustrating one learned model for inferring a high image-quality high-energy image $Im_H$' and a high image-quality low-energy image $Im_L$' from a low image-quality high-energy image $Im_H$ and a low image-quality low-energy image $Im_L$.

In this case, a low image-quality high-energy image $Im_H$ and a low image-quality low-energy image $Im_L$ are used as the input data of the training data, and a high image-quality high-energy image $Im_H$' and a high image-quality low-energy image $Im_L$ are used as the output data of the training data. More specifically, a high-energy image $Im_H$ and a low-energy image $Im_L$ captured with a low dose are used as the input data of the training data. Also, a high-energy image $Im_H$' and a low-energy image $Im_L$' captured with a high dose are used as the output data of the training data. A high-energy image $Im_H$' and a low-energy image $Im_L$' obtained by performing averaging processing or statistical processing such as the MAP estimation processing on a plurality of high-energy images $Im_H$ and low-energy images $Im_L$ may be used as the output data of the training data.

In a case such an image-quality improving model is used, the processing unit 133 uses the high image-quality high-energy image $Im_H$' and the high image-quality low-energy image $Im_L$' output from the image-quality improving model for signal processing of the energy-subtraction processing as described above. Thus, the processing unit 133 can generate, by using the image-quality improving model, the high image-quality bone image $Im_B$ and the high image-quality soft tissue image $Im_S$ based on the low image-quality high-energy image $Im_H$ and the low image-quality low-energy image $Im_L$.

Further, FIG. 8C is a diagram for illustrating two learned models that infer an energy-image of which the image-quality is improved, for the respective energy images which are the input of the energy-subtraction processing. Specifically, a learned model for inferring a high image-quality high-energy image $Im_H$' from a low image-quality high-energy image $Im_H$ and a learned model for inferring a high image-quality low-energy image $Im_L$' from a low image-quality low-energy image $Im_L$ are shown.

In this case, for the training data of a learned model for inferring a high image-quality high-energy Image $Im_H$' from a low image-quality high-energy Image $Im_H$, a low image-quality high-energy Image $Im_H$ is used as the input data and a high image-quality high-energy Image $Im_H$' is used as the output data. Further, for the training data of a learned model for inferring a high image-quality low-energy image $Im_L$' from a low image-quality low-energy Image $Im_L$, a low image-quality low-energy Image $Im_L$ is used as the input data and a high image-quality low-energy image $Im_L$' is used as the output data. Note that the low image-quality high-energy image $Im_H$, the low image-quality low-energy Image $Im_L$, the high image-quality high-energy Image $Im_H$', and the high image-quality low-energy Image $Im_L$' used as the training data may be generated in a manner similar to the manner in the above example.

In a case where such an image-quality improving model is used, the processing unit 133 uses the high image-quality high-energy image $Im_H$' and the high image-quality low-energy image $Im_L$' output from the respective image-quality improving models for the signal processing of the energy-subtraction processing as described above. Thus, the processing unit 133 can generate, by using two image quality improving models, the high-image-quality bone image $Im_B$ and the high-image-quality soft tissue image $Im_S$ based on the low image-quality high-energy image $Im_H$ and the low image-quality low-energy image $Im_L$.

Figure 8D:
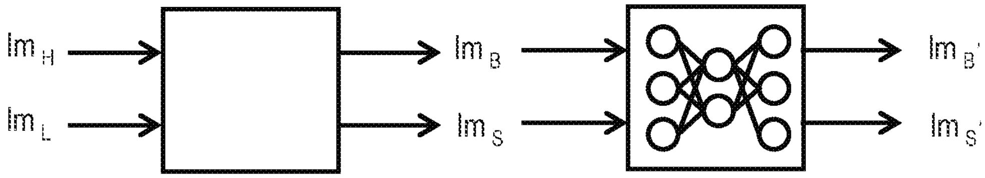
FIG. 8D is a block diagram for illustrating an example of the generation processing of the energy-subtraction images according to the first embodiment.

Further, a model for inferring a high-image-quality bone image $Im_B$' and a high image-quality soft tissue image $Im_S$' from a low image-quality bone image $Im_B$ and a low image-quality soft tissue image $Im_S$ as shown in FIG. 8D may be constructed. FIG. 8D is a diagram for illustrating one learned model for inferring a high-image-quality bone image $Im_B$' and a high image-quality soft tissue image $Im_S$' from a low-image-quality bone image $Im_B$ and a low image-quality soft tissue image $Im_S$.

In this case, a low image-quality bone image $Im_B$ and a low image-quality soft tissue image $Im_S$ are used as the input data of the training data, and a high image-quality bone image $Im_B$' and a high image-quality soft tissue image $Im_S$' are used as the output data of the training data. More specifically, a low image-quality bone image $Im_B$ and a low image-quality soft tissue image $Im_S$ generated by the above-described signal processing of the energy-subtraction processing using a high-energy image $Im_H$ and a low-energy image $Im_L$ captured with a low dose are used as the input data of the training data. Further, a high image-quality bone image $Im_B$' and a high image-quality soft tissue image $Im_S$' generated by the above-described signal processing of the energy-subtraction processing using a high image-quality high-energy image $Im_H$' and a high image-quality low-energy image $Im_L$' captured with a high dose are used as the output data of the training data.

Note that a high image-quality bone image $Im_B$' and the high image-quality soft tissue image $Im_S$' generated by the signal processing of the energy-subtraction processing using a high-energy image $Im_H$' and a low-energy image $Im_L$ obtained by performing averaging processing or the like may be the output data of the training data. Further, a high image-quality bone image $Im_B$' and a high image-quality soft tissue image $Im_S$' obtained by performing averaging processing or the like on a low image-quality bone image $Im_B$ and a low image-quality soft tissue image $Im_S$ may be used as the output data of the training data.

In a case where such an image-quality improving model is used, the processing unit 133 uses a low image-quality bone image $Im_B$ and a low image-quality soft tissue image $Im_S$ calculated from a low image-quality high-energy image $Im_H$ and a low image-quality low-energy image $Im_L$ as the input data of the image-quality improving model. The processing unit 133 can then obtain a high image-quality bone image $Im_B$ and a high image-quality soft tissue image $Im_S$ output from the image-quality improving model.

Such an image-quality improving model does not perform the image-quality improving processing on the low image-quality bone image $Im_B$ and the low image-quality soft tissue image $Im_S$ individually, but uses the both of the low image-quality bone image $Im_B$ and the low image-quality soft tissue image $Im_S$ as the input data to infer the both of the high image-quality bone image $Im_B$' and the high image-quality soft tissue image $Im_S$'. Here, since the bone image $Im_B$ and the soft tissue image $Im_S$ are correlated with each other, such a learned model may be a model for reducing the noises correlated with each other of the low image-quality bone image $Im_B$ and the low image-quality soft tissue image $Im_S$.

In addition, learned models for each imaging site may be prepared as the image-quality improving model, or may be combined them into one learned model. In a case where models for each imaging site are prepared, for example, the aforementioned learned model for recognizing the imaging site may be prepared. In this case, the processing unit 133 first infer, by using the learned model for recognizing the imaging site, the imaging site from an energy image or the like that is an input image. Then, the processing unit 133 can perform the energy-subtraction processing using the image-quality improving model corresponding to the imaging site that has been inferred. Moreover, the processing unit 133 may select an image-quality improving model to be used for the energy-subtraction processing based on the imaging site which has been input at the time of imaging.

In the above example, a configuration in which a low-image-quality energy image, which is used as the training data of the image-quality improving model, is obtained by imaging is described. In contrast, a low-image-quality energy image may be obtained by adding an artificially generated noise (artificial noise) to a high-image-quality energy image. Hereinafter, a method for generating the artificial noise added to the high image-quality energy image to generate a low image-quality energy image is described.

Figure 9:
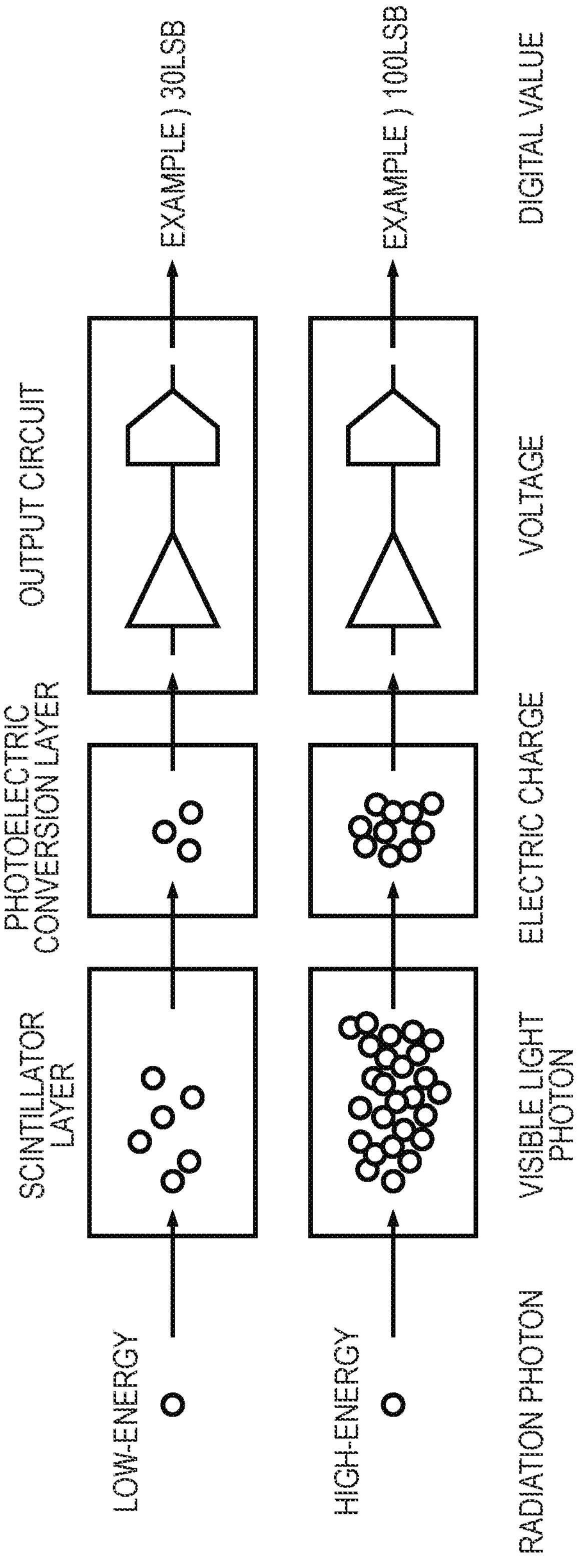
FIG. 9 is a diagram for illustrating the relationship between an energy of a radiation photon and sensor output.

FIG. 9 is a diagram for illustrating the relationship between the energy of radiation photon and the sensor output according to the first embodiment. The radiation imaging apparatus 104 includes a scintillator layer (scintillator 105) that converts a radiation into visible light photons, a photoelectric conversion layer (a two-dimensional detector 106) that converts visible light photons into electrical charges, and an output circuit that converts the electrical charges into voltages and converts them into a digital value. When the radiation photons are absorbed by the scintillator layer, visible light photons are generated in the scintillator layer. The number of the visible light photons generated at this time varies depending on the energy of the radiation photons absorbed by the scintillator layer. Specifically, the higher the energy of radiation photons is absorbed by the scintillator layer, the more visible light photons are generated. Further, the number of the electrical charges generated in the photoelectric conversion layer is determined depending on the number of the visible light photons. The final output digital value is a digital value that is obtained by converting the voltage into which the amount of this electrical charges is converted.

To perform spectral imaging, a radiation imaging apparatus 104 is irradiated with a radiation and a plurality of images are obtained. Here, it is assumed that the plurality of imaging to obtain a plurality of images are performed in a short period of time, during which the subject does not move. Further, assuming that the subject is uniform, any range including a plurality of pixels in the plurality of images is selected. In this case, the pixel values should ideally be constant within the selected range, but variation of the pixel values occurs in practice. This variation includes an electronic circuit noise (system noise) and a quantum noise according to fluctuation in the number of the radiation photons reaching the scintillator surface. For the sake of simplicity, the following description will ignore the system noise.

The number of the radiation photons reaching the scintillator layer fluctuates according to the Poisson distribution. If the Poisson distribution has a parameter of λ, the mean of the number of the radiation photons is λ and the variance is λ. If the number of the radiation photons is large enough, the Poisson distribution having the parameter λ can be approximated by a Gaussian distribution with the mean λ and the standard deviation √λ. Further, the number of the radiation photons reaching the scintillator layer is proportional to the signal component I(x, y) of each pixel. Therefore, the noise component N(x, y) of each pixel can be calculated by the following equation (10).

$$N(x, y) = \text{Random} \times \sqrt{I(x, y)} \tag{10}$$

Here, "Random" is a random number following a Gaussian distribution generated with a mean value m (=0) and a standard deviation σ. In practice, processing of convolving the noise components of peripheral pixels by a Point Spread Function (PSF) considering MTF (Modulation Transfer Function) property may be added as shown in the following equation (11). The PSF and the value of a may be set in advance as parameters corresponding to the tube voltage, the tube current, the exposure time, and the distance at the time of imaging, the configuration of radiation imaging system, etc.

$$N'(x, y) = \int\int PSF \times N(x, y)dxdy \tag{11}$$

By adding the artificial noise calculated in this manner to a high image-quality energy image I described later, a low image-quality energy image I' captured with a low dose can be generated according to the following equation (12).

$$I'(x, y) = I(x, y) + N'(x, y) \tag{12}$$

By using such an artificial noise to generate a low image-quality energy image, it is unnecessary to capture a low image-quality image to generate the training data. Therefore, the training data of the image-quality improving model, that it is difficult to generate a large amount of data due to factors such as increase of the radiation exposure, can be generated more easily.

Specifically, if a high image-quality energy image is obtained by performing imaging with a high dose, a low image-quality energy image can be generated by adding the artificial noise to the obtained high image-quality energy image. Further, a high image-quality energy-subtraction image can be generated by applying the signal processing of the energy-subtraction processing to the obtained high image-quality energy image. Furthermore, in a case where a low image-quality energy image is generated using the artificial noise, a low image-quality energy-subtraction image can be generated by performing the signal processing of the energy-subtraction processing on the generated low image-quality energy image.

Therefore, the generation of the training data can be facilitated not only for an image-quality improving model that has obtained by training using a low image-quality energy image as the input data and a high image-quality energy-subtraction image as the output data, but also for an image-quality improving model for improving the image-quality of an energy image. Similarly, the generation of training data can be facilitated for an image-quality improving model for improving the image-quality of an energy-subtraction image.

For the image-quality improving model for improving the image-quality of the energy image, training may be performed using training data obtained by applying the artificial noise to a low image-quality energy image as the input data and by applying a different artificial noise to a high image-quality energy image as the output data. By performing training in this manner, it is expected that a model for appropriately removing the noise pattern for a high image-quality image can be generated.

Figure 10:
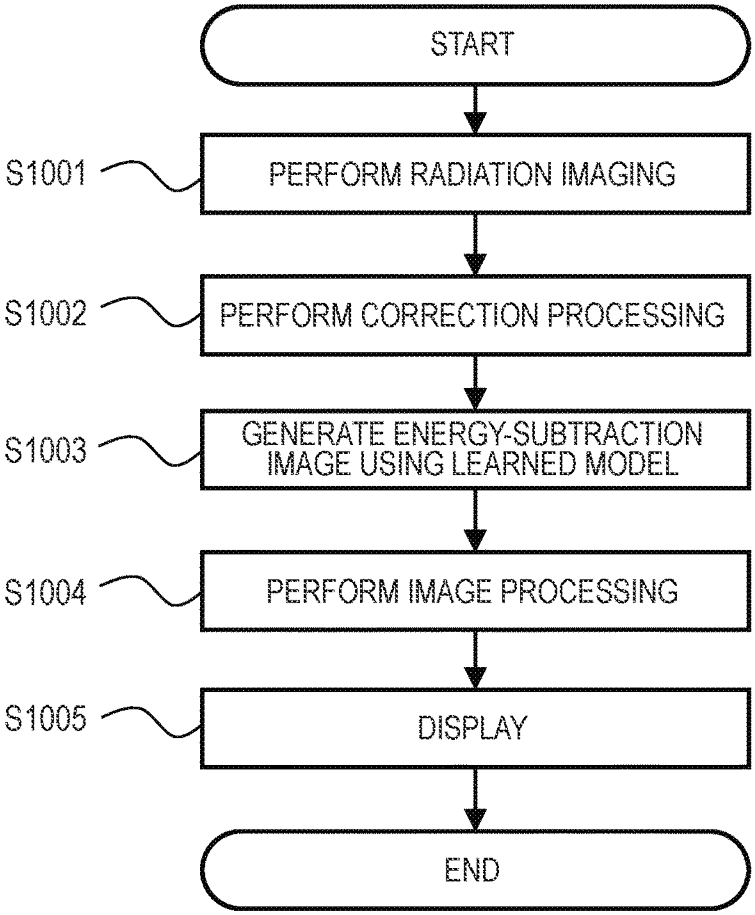
FIG. 10 is a flow chart for illustrating a series of imaging processes according to the first embodiment.

Next, a series of imaging processes according to the first embodiment will be described with reference to FIG. 10. FIG. 10 is a flow chart for illustrating a series of imaging processes according to the first embodiment. First, when the imaging process is started in response to an operation by an operator, the process moves to step S1001.

In step S1001, the radiation imaging is performed based on the imaging-condition or the like set in response to an operation by the operator. Specifically, the controlling apparatus 103 sets the imaging-condition in response to the operation by the operator via the input unit 150. The radiation controlling apparatus 102 controls the radiation generating apparatus 101 based on the imaging-condition set by the controlling apparatus 103. The radiation generating apparatus 101 irradiates a radiation toward a subject to be examined Su and the radiation imaging apparatus 104 based on the control by the radiation controlling apparatus 102. The radiation imaging apparatus 104 detects the radiation transmitted through the subject to be examined Su and transmits the image information to the controlling apparatus 103. The obtaining unit 131 of the controlling apparatus 103 obtains the image information transmitted from the radiation imaging apparatus 104.

In step S1002, the generating unit 132 performs the correction processing including the offset correction, the color correction and the gain correction described above based on the image information obtained by the obtaining unit 131 to generate a high-energy image $Im_H$ and a low-energy image $Im_L$. Note that the images W_odd and W_Even when the subject is not placed and the images F_Odd and F_Even when the X-ray is not irradiated, which are used for the correction processing, may be captured prior to the imaging of the image of the subject to be examined Su in step S1001. These images may be captured in a given imaging-condition and stored in the storage 135 in advance.

In step S1003, the processing unit 133 generates a bone image $Im_B$ and a soft tissue image $Im_S$, which are high image-quality energy-subtraction images, based on a high-energy image $Im_H$ and a low-energy image $Im_L$ using the image-quality improving model which is a learned model. Specifically, the processing unit 133 obtains and generates the high image-quality bone image $Im_B$ and the high image-quality soft tissue image $Im_S$ as the output data of the image-quality improving model by inputting the high-energy image $Im_H$ and the low-energy image $Im_L$ as the input data of the image-quality improving model.

Note that the processing unit 133 may use the image-quality improving model for improving the image-quality of the energy images as described above. In this case, the processing unit 133 obtains and generates the high image-quality high-energy image $Im_H'$ and the high image-quality low-energy image $Im_L'$ as the output data of the image-quality improving model by inputting the high-energy image $Im_H$ and the low-energy image $Im_L$ as the input data of the image-quality improving model. Then, the processing unit 133 performs the signal processing of the energy-subtraction processing on the generated high-image-quality high-energy image $Im_H'$ and the generated high image-quality low-energy image $Im_L'$ to generate the high image-quality bone image $Im_B$ and the high image-quality soft tissue image $Im_S$. In this case, the image-quality improving model to be used may be one image-quality improving model for improving the image-quality of the both of the high-energy image $Im_H$ and the low-energy image $Im_L$. Alternatively, the image-quality improving model to be used may be two image-quality improving models for improving the respective image-quality of the high-energy image $Im_H$ and low-energy image $Im_L$.

Further, the processing unit 133 may use image-quality improving model for improving the image-quality of the energy-subtraction image as described above. In this case, the processing unit 133 performs the energy-subtraction processing on the high-energy image $Im_H$ and the low-energy image $Im_L$ to generate a bone image $Im_B$ and a soft tissue image $Im_S$. Then, the processing unit 133 obtains and generates a high image-quality bone image $Im_B'$ and a high image-quality soft tissue image $Im_S'$ as the output data of the image-quality improving model by inputting the bone image $Im_B$ and the soft tissue image $Im_S$ as the input data of the image-quality improving model.

In step S1004, the processing unit 133 performs the image processing such as contrast adjustment and image size adjustment on the bone image $Im_B$ and the soft tissue image $Im_S$, which are high image-quality energy-subtraction images generated in step S1003. Note that any known method may be used as the adjustment method. Further, the processing unit 133 may apply, for example, a time-directional filter such as a recursive filter or a spatial-directional filter such as a Gaussian filter to the bone image $Im_B$ and the soft tissue image $Im_S$. Furthermore, the processing unit 133 may generate a virtual monochromatic image described below from the bone image $Im_B$ and the soft tissue image $Im_S$. The processing unit 133 may also generate a DSA image of bone and soft tissue using the high image-quality bone image $Im_B$ and the high image-quality soft tissue image $Im_S$.

In step S1005, the display controlling unit 134 causes the display unit 120 to display the imaged bone image $Im_B$ and the soft tissue image $Im_S$, etc. Note that the display controlling unit 134 may cause the display unit 120 to display high image-quality $Im_B$ and the high image-quality soft tissue image $Im_S$ side by side, or to switch each of these images to be displayed. The display controlling unit 134 may cause the display unit 120 to switch the display between the high image-quality bone image $Im_B$ and the high image-quality soft tissue image $Im_S$ and the low image-quality bone image and the low image-quality soft tissue image which are obtained by performing the energy-subtraction processing on the high-energy image $Im_H$ and the low-energy image $Im_L$. In this case, the display controlling unit 134 may collectively perform the switch of the display of these images according to an instruction from the operator via the input unit 150. In a case where the virtual monochromatic image or the DSA image is generated in step S1004, the display controlling unit 134 can cause the display unit 120 to display the generated virtual monochromatic image or the DSA image.

When the processing in step S1005 is completed, the series of the imaging processing according to the first embodiment ends. In the first embodiment, the obtaining unit 131 obtains the image information from the radiation imaging apparatus 104, the generating unit 132 performs the correction processing, and the obtaining unit 131 obtains the high-energy image $Im_H$ and the low-energy image $Im_L$ generated by the generating unit 132. On the other hand, the obtaining unit 131 may obtain the high-energy image $Im_H$ and the low-energy image $Im_L$ stored in the storage 135, or the high-energy image $Im_H$ and the low-energy image $Im_L$ from an external apparatus connected to the controlling apparatus 103. The obtaining unit 131 may also obtain the image information captured on the subject to be examined Su or the image information used for the correction processing, from the storage 135 or an external apparatus. In addition, the image processing is performed in step S1004, however in step S1005, the bone image $Im_B$ and the soft tissue image $Im_S$ for which the image processing has not been performed may be simply displayed.

As described above, the controlling apparatus 103 according to the first embodiment functions as an example of an image processing apparatus comprising the obtaining unit 131 and the processing unit 133. The obtaining unit 131 functions as an example of an obtaining unit that obtains a high-energy image $Im_H$ and a low-energy image $Im_L$, which are a plurality of images relating to different radiation energies. The processing unit 133 functions as an example of a generating unit that generates at least one of energy-subtraction images based on the high-energy image $Im_H$ and the low-energy image $Im_L$ using the image-quality improving model, which is a learned model obtained using a first image obtained using a radiation and a second image obtained by improving the image-quality of the first image.

More specifically, the processing unit 133 obtains the at least one of energy-subtraction images as the output data from the image-quality improving model by inputting the obtained high-energy image $Im_H$ and low-energy image $Im_L$ as the input data of the image-quality improving model. The energy-subtraction image may include, for example, a plurality of material decomposition images discriminating a plurality of materials. The plurality of material decomposition images may be, for example, an image indicating thickness of bone and an image indicating thickness of soft tissue, or an image indicating thickness of a contrast medium and an image indicating thickness of water. Note that the image-quality improving model may have a plurality of input channels into which a respective plurality of images is input.

In another configuration example, the processing unit 133 may obtain the high-energy image $Im_H'$ and the low-energy image $Im_L'$ with higher imager-quality than the high-energy image $Im_H$ and the low-energy image $Im_L$ as the output data from the image-quality improving model by inputting the high-energy image $Im_H$ and the low-energy image $Im_L$ as the input data of the image-quality improving model. In this case, the processing unit 133 may generate the at least one of energy-subtraction images from the high image-quality high-energy image $Im_H'$ and the high image-quality low-energy image $Im_L'$. The image-quality improving model may include a plurality of learned models corresponding to each of the high-energy image $Im_H$ and the low-energy image $Im_L$ used the as input data for image-quality improving model.

Furthermore, in other configuration examples, the processing unit 133 may generate at least one of first energy-subtraction images from the high-energy image $Im_H$ and the low-energy image $Im_L$. In this case, the processing unit 133 may obtain at least one of second energy-subtraction images with higher image-quality than the at least one of first energy-subtraction images as the output data from the image-quality improving model by inputting the at least one of first energy-subtraction images as the input data of the image-quality improving model.

The second image may be either an image obtained using a dose higher than a dose used to obtain the first image, or an image obtained by performing averaging processing or estimation processing of maximum a posteriori using the first image. In another example, the image-quality improving model may be a learned model that is obtained using a second image obtained by adding a noise which has been artificially calculated to the first image obtained by using the radiation.

According to the above configuration, the controlling apparatus 103 according to the first embodiment can generate at least one of energy-subtraction images with high image-quality using different energy images captured with low doses. Therefore, the at least one of energy-subtraction images with high image-quality can be generated while reducing the radiation dose used for examination.

The obtaining unit 131 may function as an example of an obtaining unit that obtains a plurality of first images obtained by irradiating radiation with different energies. Further, the processing unit 133 may function as an example of a generating unit that obtains a plurality of second images with higher image-quality than the plurality of first images as the output data from the image-quality improving model by inputting the plurality of first images as the input data of the image-quality improving model, and generates at least one of energy-subtraction images using the plurality of second images. In this case, the control unit 103 according to the first embodiment also can generate at least one of high image-quality energy-subtraction images using different energy images captured with a low dose. Therefore, at least one of energy-subtraction images with high image-quality can be generated while reducing the radiation dose used for examination.

It is known that the characteristics of an energy image change according to the energy to be used. Therefore, in a case where the energy image is used as the input data of the image-quality improving model in the first embodiment, it is necessary to prepare an image-quality improving model corresponding to the dose or the tube voltage at the time of imaging. For this reason, for example, the tube voltage at the time of radiation is set to a predetermined voltage in advance, and an image-quality improving model obtained by training using a training data corresponding to the tube voltage may be prepared. Further, with regard to the tube voltage at the time of radiation imaging, several patterns for pairs of a high voltage corresponding to a high-energy and a low voltage corresponding to a low-energy are prepared, and a plurality of image-quality improving models obtained by training using training data corresponding to the respective patterns. In this case, the processing unit 133 can select and use an image-quality improving model corresponding to the tube voltage of the pattern selected at the time of radiation imaging.

Second Embodiment

Next, a radiation imaging system including an image-quality improving model according to a second embodiment of the present disclosure will be described in detail with reference to FIG. 11 to FIG. 16B. Since the configuration of the image processing system according to the second embodiment is the same as the configuration of the image processing system according to the first embodiment, the same reference numbers are used for the components and the description thereof is omitted. Hereinafter, the image processing system according to the second embodiment will be described, focusing on the differences from the image processing system according to the first embodiment.

In the first embodiment, a method of inferring the high image-quality bone image $Im_B$ and the high image-quality soft tissue image $Im_S$ based on the low-quality energy images by the image-quality improving model using a deep training is described. On the other hand, in the second embodiment, a configuration for generating a virtual monochromatic image from energy-subtraction images with low image-quality and generating energy-subtraction images with high image-quality using the virtual monochromatic image is described.

As described above, in a case where an energy image is used as the input data to image-quality improving model, it is necessary to prepare a learned model corresponding to the dose or the tube voltage at the time of imaging. In contrast, a virtual monochromatic image can be generated with respect to the desired energy. Therefore, in a case where a virtual monochromatic image is used as the input data, it suffices to prepare an image-quality improving model corresponding to an energy $E_V$ of a virtual monochromatic X-ray which is set in advance. Thus, the image-quality improving model can be used regardless of the value of the tube voltage used for radiation imaging.

Figure 11:
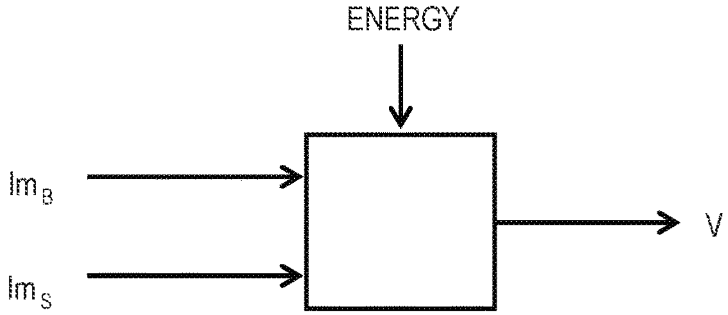
FIG. 11 is a block diagram of signal processing for generating virtual monochromatic images.

First, the virtual monochromatic image will be described with reference to FIG. 11. FIG. 11 is a block diagram of signal processing for generating the virtual monochromatic image according to the second embodiment. In the second embodiment, the virtual monochromatic image is generated from a bone image $Im_B$ and a soft tissue image $Im_S$ generated by the signal processing of the energy-subtraction processing. The virtual monochromatic image is an image that is supposed to be obtained when an X-ray of a single energy is irradiated. The virtual monochromatic image is used in Dual Energy CT, which combines the energy-subtraction processing and three-dimensional reconstruction. In the virtual monochromatic image, beam hardening artifacts and metal artifacts can be suppressed. For example, if the energy of a virtual monochromatic X-ray is $E_V$, the virtual monochromatic image V is obtained by the following equation (13).

$$V = \exp\{-\mu_B(E_V)B - \mu_S(E_v)S\} \tag{13}$$

By changing the energy $E_V$ of the virtual monochromatic X-ray, the CNR (contrast-to-noise ratio) of the virtual monochromatic image can be improved. For example, the linear attenuation coefficient μB(E) of bone is greater than the linear attenuation coefficient μS(E) of soft tissue. However, the larger the energy $E_V$ of the virtual monochromatic X-ray becomes, the smaller the difference between the linear attenuation coefficient μB(E) of bone and the linear attenuation coefficient μS(E) of soft tissue becomes. Therefore, by setting the energy $E_V$ of the virtual monochromatic X-ray to a larger value, the noise increase of the virtual monochromatic image due to the noise of the bone image is suppressed. On the other hand, the smaller the energy E v of the virtual monochromatic X-ray becomes, the larger the difference between the linear attenuation coefficient μB(E) of the bone and the linear attenuation coefficient μS(E) of the soft tissue becomes, thus the contrast of the virtual monochromatic image is improved. In this regard, by setting the energy $E_V$ of the virtual monochromatic image to an appropriate value, the CNR of the virtual monochromatic image can be improved, and, for example, the amount of contrast medium used for radiation imaging can be reduced.

Note that a composite X-ray image cam be generated by combining a plurality of virtual monochromatic images generated with a plurality of energies $E_V$. The composite X-ray image is an image that is supposed to be obtained when X-rays of any spectrum are irradiated.

Figure 12:
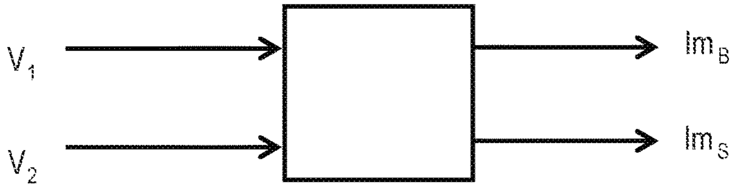
FIG. 12 is a block diagram of processing for generating energy-subtraction images from the virtual monochromatic image.

The equation (13) also allows a plurality of virtual monochromatic image $V_1$ and $V_2$ to be inversely transformed to a bone thickness B and a soft tissue thickness S. Therefore, a bone image $Im_B$ and a soft tissue image $Im_S$ can be generated by using the plurality of virtual monochromatic images $V_1$ and $V_2$ as shown in FIG. 12. Thus, in the second embodiment, at least one of energy-subtraction images with high image-quality is generated based on a plurality of virtual monochromatic images with low image-quality by using an image-quality improving model obtained by training using a plurality of virtual monochromatic images and an energy-subtraction image with high image-quality as training data.

Specifically, the processing unit 133 generates a bone image and a soft tissue image from low image-quality energy images using an existing method and transforms the generated bone image and soft tissue image into at least two virtual monochromatic images $V_H$ and $V_L$ of different energies. Then, the processing unit 133 obtains and generates, by inputting the virtual monochromatic image $V_H$ and $V_L$ as the input data of the image-quality improving model, a high image-quality bone image $Im_B$ and a high image-quality soft tissue image $Im_S$ as the output data of the image-quality improving model. In such processing, by generating the virtual monochromatic images, the noise increased by the discrimination processing (decomposition processing) using the energy-subtraction can be reduced.

Figure 13A:
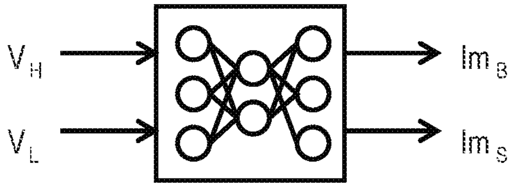
FIG. 13A is a block diagram for illustrating an example of generation processing of energy-subtraction images according to the second embodiment.
Figure 13B:
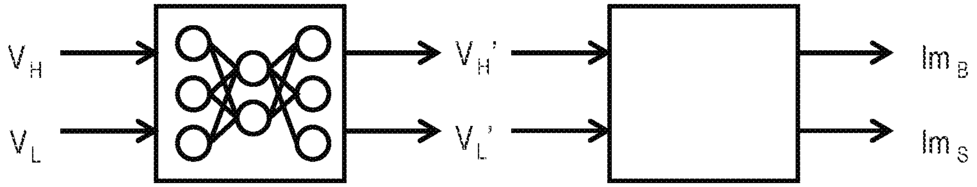
FIG. 13B is a block diagram for illustrating an example of the generation processing of the energy-subtraction images according to the second embodiment.
Figure 13C:
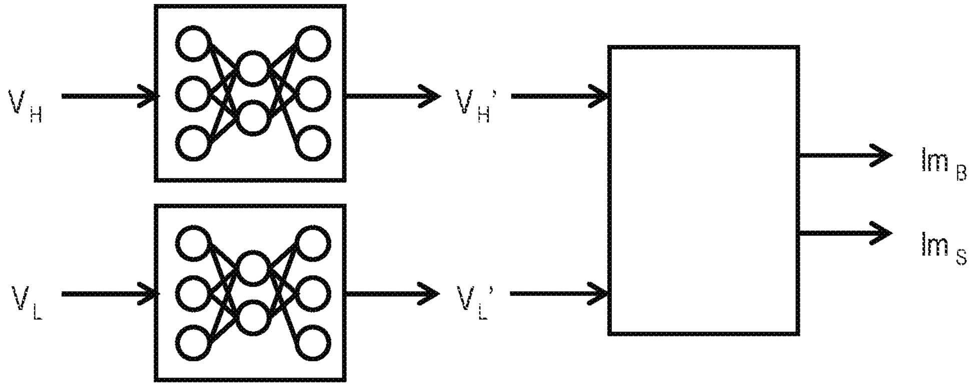
FIG. 13C is a block diagram for illustrating an example of the generation processing of the energy-subtraction images according to the second embodiment.

Next, the image-quality improving model according to the second embodiment and the other examples of the image-quality improving model will be described with reference to FIG. 13A to FIG. 13C. FIG. 13A to FIG. 13C are block diagrams for illustrating flows of a series of image processing according to the second embodiment.

First, in the image-quality improving model according to the second embodiment, the low image-quality virtual monochromatic images $V_H$, $V_L$ are set as the input data and the high image-quality bone image $Im_B$ and the high image-quality soft tissue image $Im_S$ are set as the output data as shown in FIG. 13A. For the training data of such an image-quality improving model, low image-quality virtual monochromatic images $V_H$ and $V_L$ should be used as the input data and a high image-quality bone image $Im_B$ and a high image-quality soft tissue image $Im_S$ should be used as the output data.

Here, the low image-quality virtual monochromatic images $V_H$ and $V_L$ may be generated by generating a low image-quality bone image and a low image-quality soft tissue image by the signal processing of the energy-subtraction processing from the energy images captured with a low dose, and transforming the low image-quality bone image and the low image-quality soft tissue image. Further, the low image quality virtual monochromatic image $V_H$ and $V_L$ may be obtained by adding an artificial noise to high image-quality virtual monochromatic images based on images captured with a high dose in advance, or virtual monochromatic images of which the image quality has been improved by averaging processing. The method for generating the high image-quality bone image $Im_B$ and the high image-quality soft tissue image $Im_S$ may be the same as the method for generating the high-image-quality bone image $Im_B$ and the high image-quality soft tissue image $Im_S$ described in the first embodiment.

As another example of the image-quality improving model, a learned model for improving the image quality of the virtual monochromatic image $V_H$ and $V_L$ may be used as shown in FIG. 13B and FIG. 13C. FIG. 13B shows one learned model for inferring the high image-quality virtual monochromatic images $V_H'$ and $V_L'$ from the low image-quality virtual monochromatic images $V_H$ and $V_L$.

In this case, low image-quality virtual monochromatic images $V_H$ and $V_L$ are used as the input data of the training data and high image-quality virtual monochromatic images $V_H$' and $V_L$' are used as the output data of the training data. As the high image-quality virtual monochromatic images $V_H$' and $V_L$', high image-quality virtual monochromatic images transformed from a bone image and a soft tissue image generated using a high-energy and a low-energy image captured with a high dose can be used. High image-quality virtual monochromatic images $V_H$' and $V_L$' obtained by performing averaging processing or statistical processing such as the MAP estimation processing on the plurality of virtual monochromatic image for each energy may be used as the output data of the training data.

In a case where such an image-quality improving model is used, the processing unit 133 can generate the high-image-quality bone image $Im_B$ and the high-image-quality soft tissue image $Im_S$ by performing the inverse-transform as described above for the high image-quality virtual monochromatic images $V_H$' and $V_L$' output from the image-quality improving model. Thus, the processing unit 133 can generate the high image-quality bone image $Im_B$ and the high image-quality soft tissue image $Im_S$ based on the low image-quality virtual monochromatic images $V_H$ and $V_L$ using the image-quality improving model.

Further, FIG. 13C shows two learned models for inferring virtual monochromatic image of which the image quality is improved for respective low image-quality virtual monochromatic images. Specifically, FIG. 13C shows learned model for inferring a high image-quality virtual monochromatic image $V_H$' from a low image-quality virtual monochromatic image $V_H$, and a learned model for inferring a high-image-quality virtual monochromatic image $V_L$' from a low image-quality virtual monochromatic image $V_L$.

In this case, for the training data of the learned model for inferring the high image-quality virtual monochromatic image $V_H$' from the low image-quality virtual monochromatic image $V_H$, a low image-quality virtual monochromatic image $V_H$ is used as the input data and a high image-quality virtual monochromatic image $V_H$' is used as output data. For the training data of the learned model for inferring the high-image-quality virtual monochromatic image $V_L$' from the low-image-quality virtual monochromatic image $V_L$, a low image-quality virtual monochromatic image $V_L$ is used as the input data and a high image-quality virtual monochromatic image $V_L$' is used as the output data. The low image-quality virtual monochromatic image $V_H$ and $V_L$ and high image-quality virtual monochromatic image $V_H$' and $V_L$' used as training data may be generated in a manner similar to the manner in the above example.

In a case where such an image-quality improving model is used, the processing unit 133 can generate the high-image-quality bone image $Im_B$ and the high-image-quality soft tissue image $Im_S$ by performing the inverse-transform as described above for the high image-quality virtual monochromatic images $V_H$' and $V_L$' output from each image-quality improving model. Thus, the processing unit 133 can generate the high image-quality bone image $Im_B$ and the high image-quality soft tissue image $Im_S$ based on low image-quality virtual monochromatic images $V_H$ and $V_L$ using the two image-quality improving models.

As for the image-quality improving model for improving the image quality of the virtual monochromatic image as shown in FIG. 13B and FIG. 13C, it is also possible to perform training using data in which different artificial noises are added to each of the input data and the output data.

By constructing the learned model in this manner, it is possible to construct an image-quality improving model independent of the setting of the tube voltage at the time of imaging. Further, by using the virtual monochromatic images, it is possible to generate high image-quality bone image and the high image-quality soft tissue image while suppressing the effect of the noise generated when performing the material decomposition of the energy images to generate the bone image and the soft tissue image.

Figure 14:
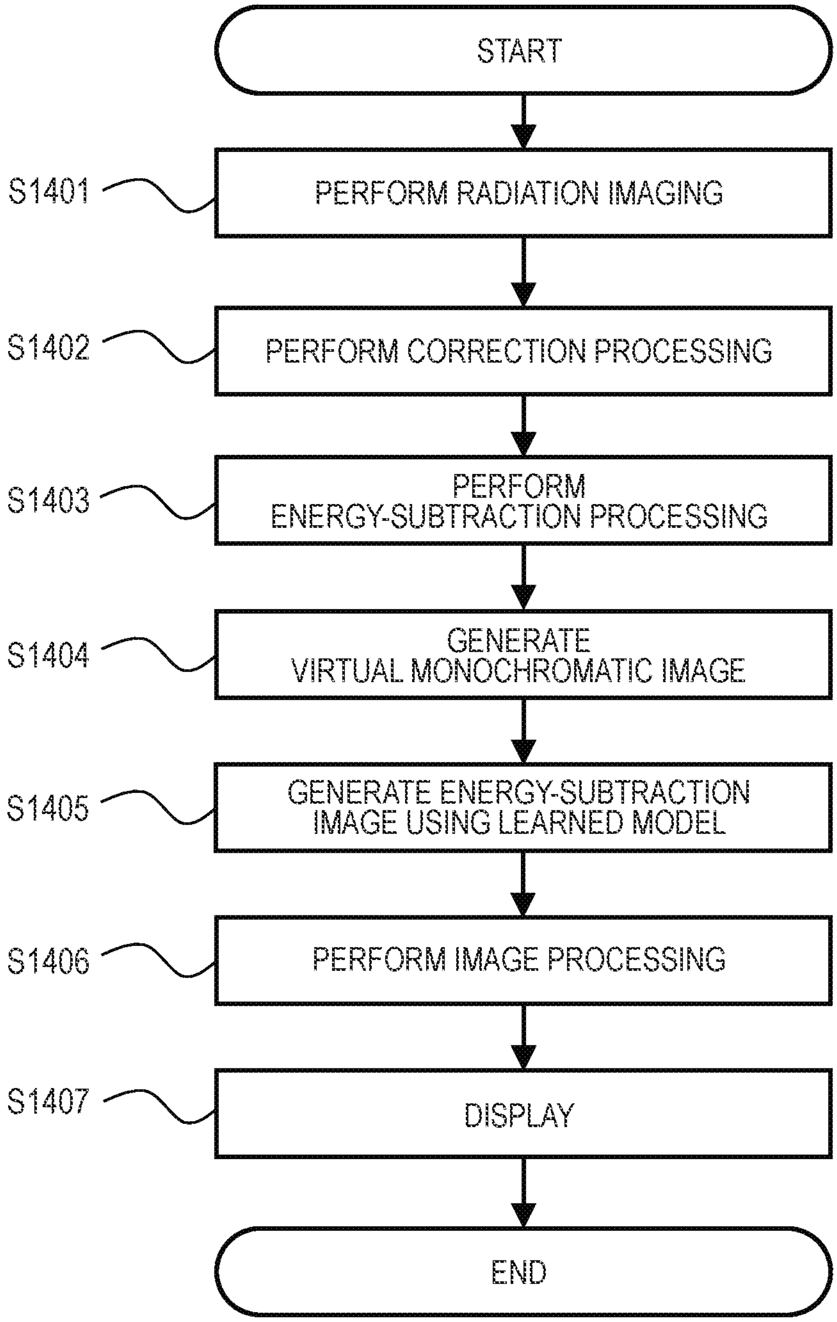
FIG. 14 is a flowchart for illustrating a series of imaging processing according to the second embodiment.

Next, a series of imaging processes according to the second embodiment will be described with reference to FIG. 14. FIG. 14 is a flowchart or illustrating the series of imaging processes according to the second embodiment. The processes of steps S1401, S1402, S1406 and S1407 according to the second embodiment are the same as the processes of steps S1001, S1002, S1004 and S1005 according to the first embodiment. Therefore, the description of these steps will be omitted below, and a description of the series of imaging processes according to the second embodiment will be focused on the differences from the processes according to the first embodiment.

In the series of imaging processes according to the second embodiment, the process is started, and if the processes of steps S1401 and S1402 are completed, the process proceeds to step S1403. In step S1403, the processing unit 133 generates a bone image and a soft tissue image by performing the signal processing of the existing energy-subtraction processing on a high-energy image $Im_H$ and a low-energy image $Im_L$ obtained in step S1402. For the signal processing of the existing energy-subtraction processing, the processes described using the equations (3) to (9) may be used.

In step S1404, the processing unit 133 generates virtual monochromatic images $V_H$, and $V_L$ of different energies using the bone image and the soft tissue image generated in step S1403. The energies of the virtual monochromatic images may correspond to the energies of virtual monochromatic images used as the training data of the image-quality improving model. The energy of the virtual monochromatic image used as the training data may be set freely. For example, the energy of the virtual monochromatic image can be set considering the CNR of the virtual monochromatic image.

In step S1405, the processing unit 133 generates, by using the image-quality improving model as a learned model, a bone image $Im_B$ and a soft tissue image $Im_S$ which are high image-quality energy-subtraction images based on the virtual monochromatic images $V_H$, and $V_L$ generated in step S1404. Specifically, the processing unit 133 obtains and generates a high image-quality bone image $Im_B$ and a high image-quality soft tissue image $Im_S$ as the output data of the image-quality improving model by inputting the virtual monochromatic images $V_H$, and $V_L$ as the input data of the image-quality improving model.

Note that the processing unit 133 may also use the image-quality improving model for improving the image quality of the virtual monochromatic image, as described above. In this case, the processing unit 133 obtains and generates the high image-quality virtual monochromatic image $V_H$', and $V_L$' as the output data of the image-quality improving model by inputting the virtual monochromatic image $V_H$, and $V_L$ as the input data of the image-quality improving model. Then, the processing unit 133 generates the high image-quality bone image $Im_B$ and the high image-quality soft tissue image $Im_S$ by performing the inverse-transform on the generated high image-quality virtual monochromatic images $V_H$', and $V_L$'. In this case, the image-quality improving model to be used may be one image-quality improving model for improving the image-quality of the both of the virtual monochromatic images $V_H$ and $V_L$.

On the other hand, the image-quality improving model to be used may be two image-quality improving models for improving the image-quality of the respective virtual monochromatic images $V_H$ and $V_L$. Since the subsequent processes are the same as the series of imaging processes in the first embodiment, the description thereof is omitted.

As described above, the processing unit 133 in second embodiment generates first energy-subtraction images from the plurality of images obtained by the obtaining unit 131, and generates a plurality of virtual monochromatic images $V_H$, and $V_L$ of different energies from the first energy-subtraction images. In addition, the processing unit 133 generates, by using the image-quality improving model, at least one of second energy-subtraction images with higher image-quality than the first energy-subtraction images based on the generated plurality of virtual monochromatic images $V_H$, and $V_L$. More specifically, the processing unit 133 obtains the second energy-subtraction images as the output data from the image-quality improving model by inputting the plurality of virtual monochromatic images $V_H$, and $V_L$ as the input data of the image-quality improving model. The image-quality improving model can have a plurality of input channels into which the respective plurality of input virtual monochromatic images $V_H$, and $V_L$ are input.

Further, in another configuration example, the processing unit 133 may obtain, by inputting the generated the plurality of virtual monochromatic images $V_H$, and $V_L$ as the input data of the image-quality improving model, a plurality of virtual monochromatic images $V_H'$, and $V_L'$ with higher image-quality than the plurality of virtual monochromatic images $V_H$, and $V_L$ as the output data from the image-quality improving model. In this case, the processing unit 133 generates the at least one of second energy-subtraction images from the plurality of virtual monochromatic images $V_H'$, and $V_L'$ obtained as the output data from the image-quality improving model. In this case, the image-quality improving model may include a plurality of learned models corresponding to the respective plurality of virtual monochromatic images $V_H$, and $V_L$ used as the input data of the image-quality improving model.

Even in a case where the above configuration is employed, at least one of energy-subtractions image with high image-quality can be generated using different energy images captured with low doses. Thus, the energy-subtraction images with high image-quality can be generated while reducing the radiation dose used for examination. Further, by using the virtual monochromatic images, at least one of energy-subtraction images with high image-quality can be generated while suppressing the effect of noise generated when discriminating materials by the energy-subtraction processing.

Figure 15A:
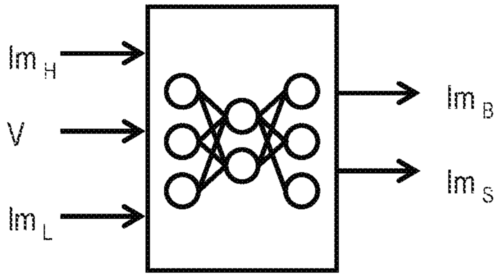
FIG. 15A is a block diagram for illustrating an example of generation processing of energy-subtraction images according to a variation of the second embodiment.

The configuration of the image-quality improving model is not limited to the configuration described in the first embodiment and the second embodiment. The combination of the input image and the output image can be changed suitably. For example, as shown in FIG. 15A, a high-energy image $Im_H$, a low-energy image $Im_L$ and a virtual monochromatic image V may be combined as the input images, and the bone image $Im_B$ and the soft tissue image $Im_S$ which are energy-subtraction images with high image-quality may be inferred using the input images.

In this case, the processing unit 133 generates the first energy-subtraction images from the high-energy image $Im_H$ and the low-energy image $Im_L$ obtained by the obtaining unit 131. Further, the processing unit 133 generates the virtual monochromatic image V from the first energy-subtraction images. The processing unit 133 can obtain, by inputting the high-energy image $Im_H$ and the low-energy image $Im_L$ obtained by the obtaining unit 131 and the generated virtual monochromatic image as the input data of the image-quality improving model, the at least one of second energy-subtraction images with higher image-quality than the first energy-subtraction image as the output data from the image-quality improving model.

For the training data in this case, a high-energy image $Im_H$ and a low-energy image $Im_L$ captured with low doses and a virtual monochromatic image obtained by transforming a bone image and a soft tissue image which are generated by performing the signal processing of the energy-subtraction processing on the energy images may be used as the input data. As the output data of the training data, a high image-quality bone image $Im_B$ and a high image-quality soft tissue image $Im_S$ generated in the same manner as the training data according to the first embodiment may be used. Further, as the input data of the training data, low image-quality energy images generated by adding an artificial noise to high image-quality energy images may be used. Similarly, as the input data of the training data, a virtual monochromatic image with low image-quality generated by adding an artificial noise to a virtual monochromatic image with high image-quality may be used.

Figure 15B:
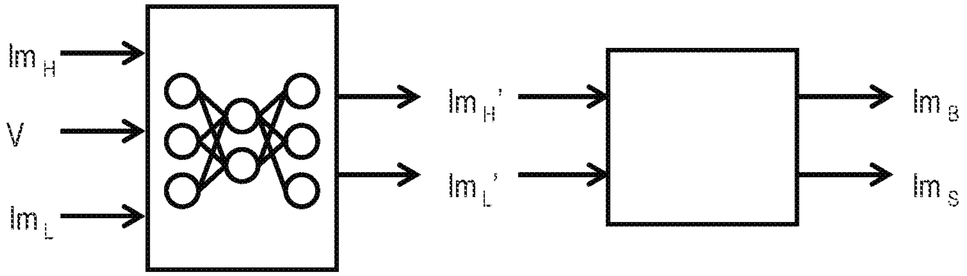
FIG. 15B is a block diagram for illustrating an example of the generation processing of the energy-subtraction images according to a variation of the second embodiment.

Furthermore, as shown in FIG. 15B, a high-energy image $Im_H$, a low-energy image $Im_L$ and a virtual monochromatic image V may be combined as input images, a high-energy image $Im_H'$ and a low-energy image $Im_L'$ with high image-quality may be inferred using the input images. In this case, the processing unit 133 obtains, by inputting the high-energy image $Im_H$ and the low-energy image $Im_L$ obtained by the obtaining unit 131 and the generated virtual monochromatic image V as the input data of the image-quality improving model, the high-energy image $Im_H'$ and the low-energy image $Im_L$ with higher image-quality than the high-energy image $Im_H$ and the low-energy image $Im_L$ the as the output data from the image-quality improving model. The processing unit 133 can generate the at least one of second energy-subtraction images with higher image-quality than the first energy-subtraction images from the high-energy image $Im_H'$ and the low-energy image $Im_L'$ obtained as the output data from the image-quality improving model.

The input data of the training data in this case may be similar to the example shown in FIG. 15A. As the output data of the training data, a high image-quality high-energy image $Im_H'$ and a high image-quality low-energy image $Im_L'$ generated in the same manner as the training data according to the first embodiment may be used.

Figure 16A:
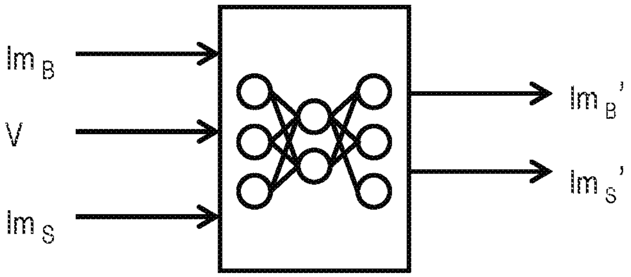
FIG. 16A is a block diagram for illustrating an example of the generation processing of the energy-subtraction images according to a variation of the second embodiment.

Further, for the model for inferring the high image-quality bone image $Im_B$ and the high image-quality soft tissue image $Im_S$ with high image-quality as the output data by using the low image-quality bone image $Im_B$ and the low image-quality soft tissue image $Im_S$ as the input data, which described in the first embodiment, a virtual monochromatic image may be added to the input data. FIG. 16A shows an image-quality improving model for inferring the high image-quality bone image $Im_B'$ and the high image-quality soft tissue image $Im_S'$ as the output data by using input data in which a low image-quality bone image $Im_B$, a low image-quality soft tissue image $Im_S$ and a virtual monochromatic image V are combined. In this case, the processing unit 133 obtains, by inputting the generated virtual monochromatic image V and at least one of the generated first energy-subtraction images as the input data of the image-quality improving model, at least one of second energy-subtraction images with higher image-quality than the first energy-subtraction images as the output data from the image-quality improving model. In such a case, by adding the virtual monochromatic image with a reduced noise generated during discrimination as the input data, it is expected that a bone image $Im_B$ and a soft tissue image $Im_S$ with higher image-quality can be inferred based on a bone image $Im_B$, a soft tissue image $Im_S$ and a virtual monochromatic image which are correlated with each other.

For the training data in this case, a bone image $Im_B$ and a soft tissue image $Im_S$ generated by the signal processing of the energy-subtraction processing on a high-energy image and a low-energy image captured with low doses, and a virtual monochromatic image V obtained by transforming the bone image $Im_B$ and the soft tissue image $Im_S$ may be used as the input data. As the output data of the training data, a high image-quality bone image $Im_B$' and a high image-quality soft tissue image $Im_S$' generated in the same manner as the training data according to the first embodiment may be used. Note that a low-image-quality virtual monochromatic image generated by adding an artificial noise to a high-image-quality virtual monochromatic image may be used as the input data of the training data.

Figure 16B:
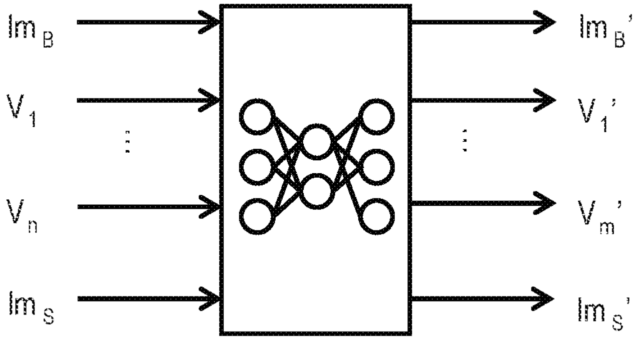
FIG. 16B is a block diagram for illustrating an example of the generation processing of the energy-subtraction images according to a variation of the second embodiment.

Furthermore, FIG. 16B is a diagram for illustrating an image-quality improving model for inferring the images of (m+2) channels from images of the total (n+2) channels for which n virtual monochromatic images are added as input images. Note that "n" and "m" do not need to coincide with each other and "m" may be 0. For the training data, a bone image $Im_B$ and a soft tissue image $Im_S$ as generated in the above-described manner, and virtual monochromatic images $V_1$-$V_n$ obtained by transforming the bone image $Im_B$ and the soft tissue image $Im_S$ may be used as the input data. Also, a high mage-quality bone image $Im_B$' and a high mage-quality soft tissue image $Im_S$' generated in the same manner as the training data according to the first embodiment, and high image-quality virtual monochromatic images $V_1$'-$V_m$' generated in the same manner as the training data according to the second embodiment may be used as the output data. Note that a low-image-quality virtual monochromatic image generated by adding an artificial noise to a high image-quality virtual monochromatic image may be used as the input data of the training data. Such an image-quality improving model is expected to become a learned model that can infer an image with high image-quality based on the correlation of each image.

Note that with respect to the image-quality improving model described in the first embodiment and the second embodiment, and the various image-quality improving models mentioned above, it is also possible to perform various modifications on the parameters, the input data, the output data, etc., while confirming the performance of the output image to be finally inferred.

Third Embodiment

The third embodiment of the present disclosure is described below with reference to FIG. 17, FIG. 18A and FIG. 18B. In the first and second embodiment, the technique of the present disclosure is applied to the radiation imaging system for imaging a medical image. In contrast, in the third embodiment, the technique of the present disclosure is applied to a radiation imaging system used in an in-line automatic examination.

In the in-line automatic examination, a technique using a tomographic image reconstructed from a plurality of projected images captured with an X-ray is widely used. For example, in the in-line automatic examination, it is desirable to conduct the examination in a state where an object to be examined (for example, a substrate with a flat shape) is arranged close to the X-ray source, for the purpose of magnification imaging. On the other hand, when X-rays are irradiated in a state where the X-ray source is arranged close to the thickness direction side of the substrate, it is difficult to transmit the X-rays in the width direction of the substrate having a long dimension as compared to the thickness, so that the desired examination result may not be obtained. In this regard, the technique of irradiate the X-rays obliquely to the object to be examined (for example, a technique called oblique CT, lamino CT, or planar CT) has been proposed. In the technique for irradiating the X-rays obliquely to the object to be examined, it is possible to bring the object close to the X-ray source, so that it is facilitated to adjust the magnification of the image and it is possible to make the size of the examination device compact.

Here, an energy-subtraction image such as a material decomposition image also can be obtained by performing the energy-subtraction processing on a plurality of projection images captured by irradiating the X-rays in the oblique direction to the object to be examined or on a tomographic image reconstructed from the projection images. However, even in such a case, the above-mentioned problems such as increase of the radiation dose due to a plurality of imaging and increase of the noise related to the imaging with a low dose occur.

Therefore, the third embodiment also has an object to provide an image processing apparatus that can generate at least one of energy-subtraction images with high image-quality while reducing the radiation dose used for examination. In this regard, the third embodiment generates, by using an image-quality improving model, at least one of energy-subtraction images with high image-quality based on a plurality of projection images captured by irradiating a radiation obliquely to an object to be examined or a tomographic image reconstructed from the projection images.

First, the configuration of a radiation imaging system according to the third embodiment will be described with reference to FIG. 17. FIG. 17 is a diagram for illustrating an example of the overall configuration of the radiation imaging system according to the third embodiment. The radiation imaging system 1700 includes a controlling apparatus 1710, a radiation generating apparatus 1701, a stage 1706, a radiation imaging apparatus 1704, a robot arm 1705, and an imaging apparatus supporter 1703. Note that the configurations of the radiation generating apparatus 1701 and the radiation imaging apparatus 1704 may be the same as the configurations of the radiation generating apparatus 101 and the radiation imaging apparatus 104 according to the first embodiment, and the description thereof is omitted.

Here, the radiation imaging apparatus 1704 is supported by the imaging apparatus supporter 1703, and the radiation imaging apparatus 1704 is configured to be movable by moving the imaging apparatus supporter 1703 and the robot arm 1705. Further, an object to be examined (hereinafter also referred to as "workpiece 1702") is arranged on the stage 1706. The stage 1706 is configured to move to a specified position for radiation imaging or to stop at a specified position for radiation imaging in accordance with a control signal from the stage controlling unit 1717 of the controlling apparatus 1710.

The object to be examined can include, for example, a human body or various articles. In a case where a human body is the object to be examined, the third embodiment can be applied to tomographic image diagnosis. In a case where various objects (for example, the substrate) are the objects to be examined, the third embodiment can be applied to the determination of the quality of the state in which electronic components are attached to the substrate and the calculation of the tomographic position within the object to be examined.

The controlling apparatus 1710 includes an obtaining unit 1711, a generating unit 1712, a processing unit 1713, a display controlling unit 1714, a storage 1715, an imaging apparatus controlling unit 1716, a stage controlling unit 1717, and a radiation controlling unit 1718. Note that the obtaining unit 1711, the display controlling unit 1714, and the storage 1715 may be the same as the obtaining unit 131, the display controlling unit 134, and the storage 135 according to the first embodiment, and the description thereof is omitted.

Here, the controlling apparatus 1710 can be configured by a computer including a processor and a memory. The controlling apparatus 1710 can be configured by a general computer or a computer dedicated to the radiation control system. For example, a personal computer, a desktop PC, a notebook PC, a tablet PC (a portable information terminal), or the like may be used for the controlling apparatus 1710. Furthermore, the controlling apparatus 1710 can be configured as a cloud-type computer in which some components are arranged in an external apparatus.

Each component of the controlling apparatus 1710 other than the storage 1715 may be configured by a software module executed by a processor such as a CPU or MPU. The processor may be, for example, a GPU, an FPGA, or the like. Each component may be configured by using a circuit or the like for performing a specific function, such as an ASIC. The storage 1715 may be configured by, for example, an optical disk such as a hard disk or any storage medium such as a memory.

A display unit 1720 and an input unit 1750 are connected to the controlling apparatus 1710. The display unit 1720 and input unit 1750 may be the same as the display unit 120 and the input unit 150 according to the first embodiment, and the description thereof is omitted.

The radiation controlling unit 1718 can function similarly to the radiation controlling apparatus 102 according to the first embodiment. The radiation controlling unit 1718 can control imaging-conditions such as the irradiation angle of the radiation, the radiation focus position, the tube voltage, and the tube current of the radiation generating apparatus 1701, etc. based on the operation by the operator via the input unit 1750.

The radiation generating apparatus 1701 outputs the radiation with an axis through the radiation focus as the central axis based on the control signal from the radiation controlling unit 1718. The radiation generating apparatus 1701 can be configured as, for example, a radiation generating apparatus movable in the XYZΦ directions. In this case, for example, the radiation generating apparatus 1701 includes a driving unit such as a motor and can moves to any position in the plane (in the XY plane) intersecting the rotation axis (Z axis) or stopped at any position (for example, the position of the rotation axis (Z axis)) based on the control signal from the radiation controlling unit 1718. The radiation generating apparatus 1701 irradiates the radiation from a direction inclined to the rotation axis in a state where the radiation generating apparatus 1701 is moved in the plane intersecting the rotation axis or in a state where the radiation generating apparatus 1701 is stopped at the position of the rotation axis.

Figure 17:
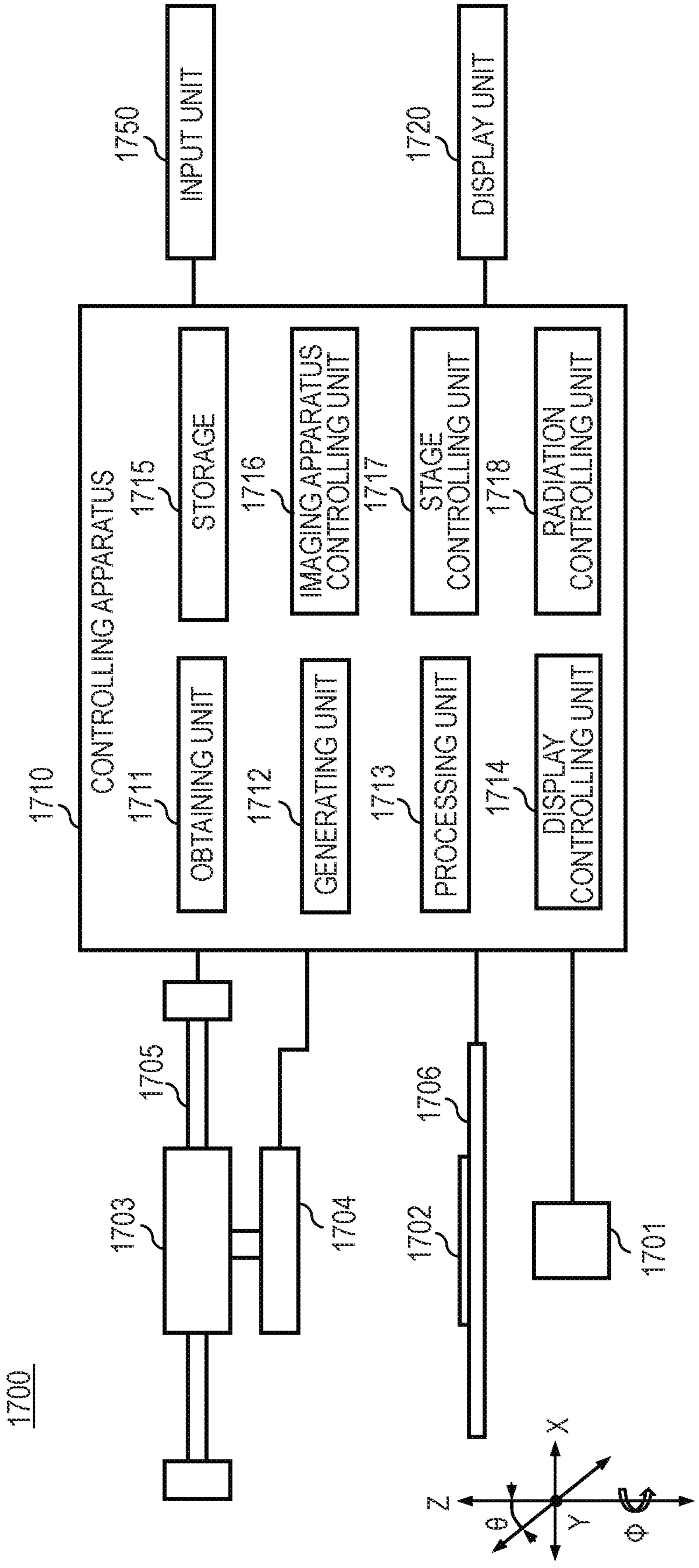
FIG. 17 is a diagram for illustrating an example of the overall configuration of a radiation imaging system according to the third embodiment.

In FIG. 17, the rotation axis is the axis in the up and down directions (Z axis) of the paper surface, and the angle θ indicates the inclination angle with respect to the rotation axis (Z axis). The angle Φ indicates the rotation angle about the Z axis. The X direction corresponds, for example, to the left and right directions of the paper surface, and the Y direction corresponds to the direction perpendicular to the paper surface. The Z direction corresponds to, for example, the up and down directions of the paper surface. The setting of the coordinate system in FIG. 17 is the same in FIG. 18A and FIG. 18B.

Figure 18A:
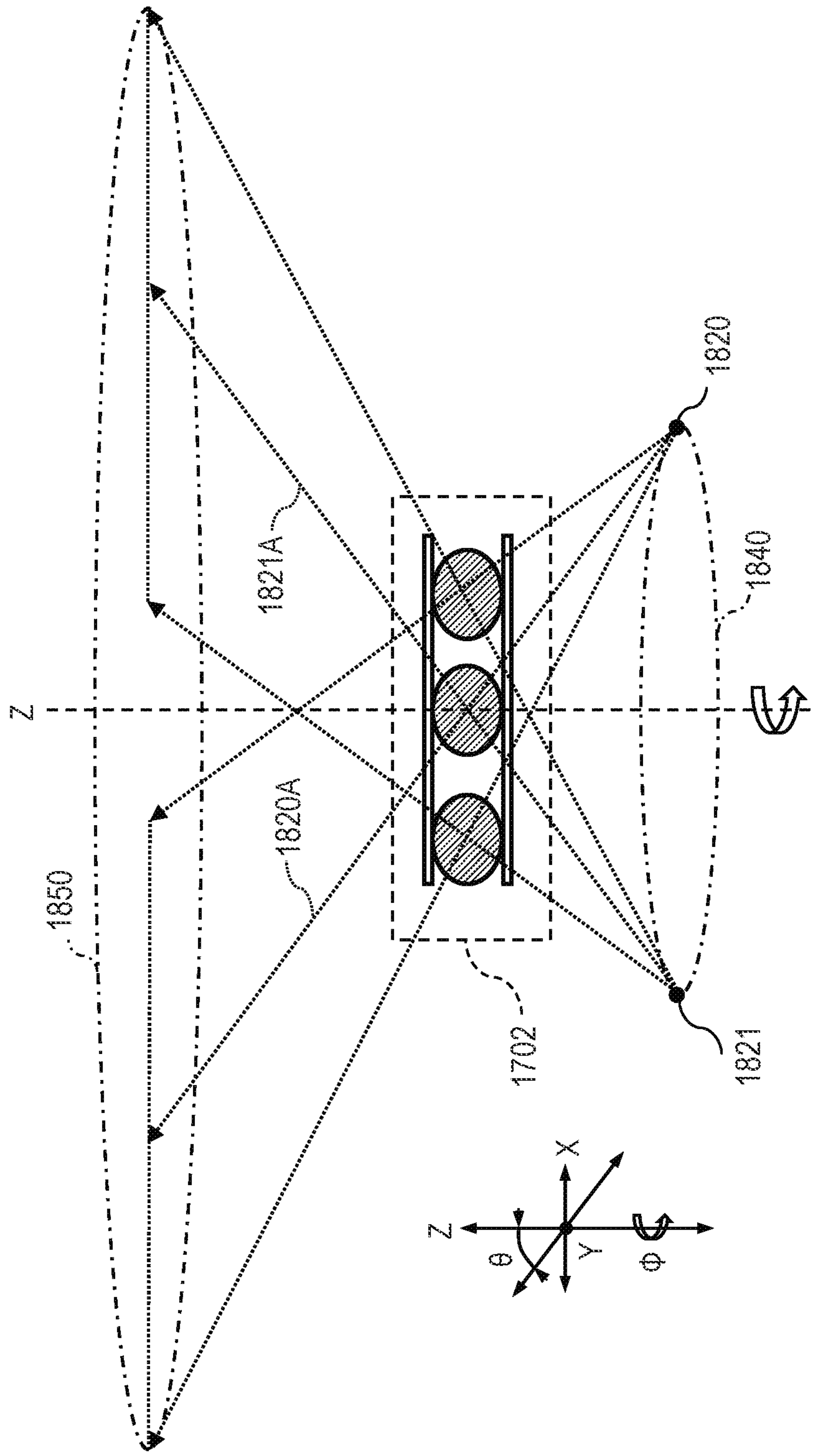
FIG. 18A is a diagram for describing an example of radiation imaging process according to the third embodiment.

The state where the radiation generating apparatus 1701 is moved in the plane intersecting the rotation axis means, for example, a state where the radiation generating apparatus 1701 is moved in the plane (in the XY plane) intersecting the rotation axis (Z axis) with a predetermined trajectory 1840, as shown in FIG. 18A. Further, the state where the radiation generating apparatus 1701 is stopped at the position of the rotation axis means, for example, a state where the radiation generating apparatus 1701 is stopped at the position of the rotation axis (Z axis) as shown in FIG. 18B. Furthermore, the irradiation of the radiation from the direction inclined with respect to the rotation axis means, for example, irradiation of the radiation in a state where the irradiation direction is inclined by the angle θ with respect to the rotation axis (Z axis) as shown in FIG. 18A and FIG. 18B.

In the radiation imaging system shown in FIG. 18A, the radiation generating apparatus 1701 is configured to be movable in the plane (in the XY plane) intersecting the rotation axis (Z axis) and irradiate the radiation from a direction inclined with respect to the rotation axis. The stage 1706 (holding unit) holding the workpiece 1702 holds the workpiece 1702 in a state where the stage 1706 is stopped at the position of the rotation axis (Z axis). The radiation imaging apparatus 1704 is configured to be movable in the plane (in the XY plane) intersecting the rotation axis (Z axis), and detect the radiation transmitted through the object to be examined. In FIG. 18A, the radiation generating apparatus 1701 outputs the radiation from the position 1820 of the radiation focus of the radiation generating apparatus 1701 with the axis 1820A through the radiation focus as the central axis based on the control signal from the radiation controlling unit 1718. Similarly, the radiation generating apparatus 1701 outputs the radiation from the position 1821 of the radiation focus of the radiation generating apparatus 1701 with the axis 1821A through the radiation focus as the central axis based on the control signal from the radiation controlling unit 1718. Here, the angle formed by the axis 1820A (axis 1821A) and the rotation axis (Z axis) is the angle of inclination (angle θ).

Figure 18B:
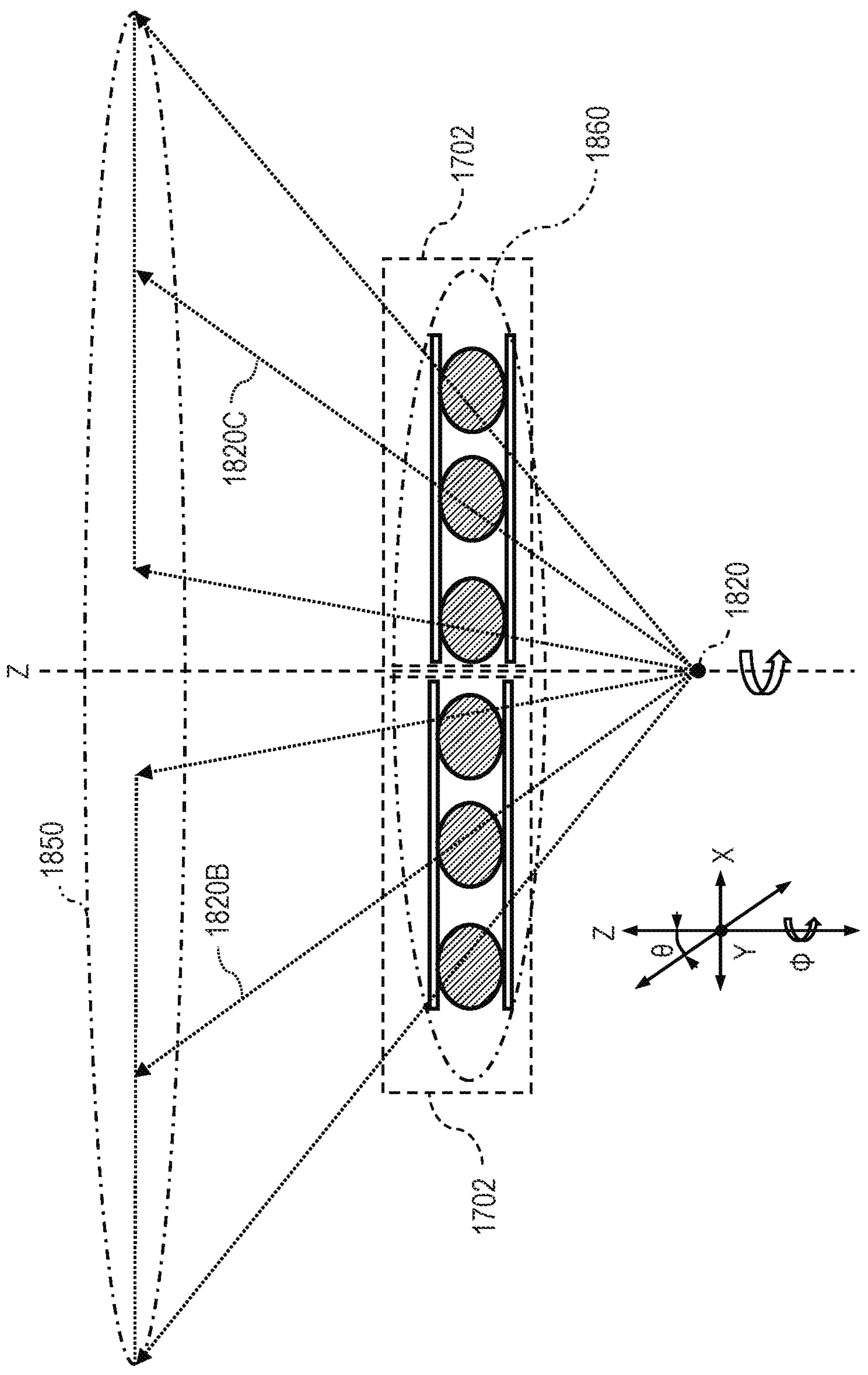
FIG. 18B is a diagram for describing an example of radiation imaging process according to the third embodiment.

On the other hand, in the radiation imaging system shown in FIG. 18B, the radiation generating apparatus 1701 irradiates the radiation from a direction inclined with respect to the rotation axis (Z-axis) in a state where the radiation generating apparatus 1701 is stopped at the position of the rotation axis. The stage 1706 holding the workpiece 1702 is configured to be movable in the plane (in the XY plane) intersecting the rotation axis and hold the workpiece 1702. The radiation imaging apparatus 1704 is configured to be movable in the plane (in the XY plane) intersecting the rotation axis (the Z axis) and detect the radiation transmitted through the object to be examined. In FIG. 18B, the radiation generating apparatus 1701 outputs the radiation with the axis 1820B through the radiation focus as the central axis from the position 1820 of the radiation focus (the position of the rotation axis (the Z axis)) of the radiation generating apparatus 1701 based on the control signal from the radiation controlling unit 1718. Further, the radiation generating apparatus 1701 changes the irradiation angle of the radiation based on the control signal from the radiation controlling unit 1718, and outputs the radiation with the axis 1820C through radiation focus as the central axis from the position 1820 of the radiation focus of the radiation generating apparatus 1701. Here, the angle formed by the axis 1820B (axis 1821C) and the rotation axis (Z axis) is the angle of inclination (angle θ).

The stage controlling unit 1717 performs the position control of the stage 1706 to move the stage 1706 to a specified position for the radiation imaging or to stop the stage 1706 in a predetermined position for the radiation photography. Note that, the stage controlling unit 1717 can perform the position control of the stage 1706 based on a program for a specified imaging operation or an operation by the operator.

A workpiece 1702, which is an object to be examined, is held on the stage 1706. The stage 1706 is configured as a stage is movable, for example, in the XYZΦ direction. The stage 1706 includes, for example, a driving unit such as a motor and can be moved to any position in the plane (in the XY plane) intersecting the rotation axis (Z axis) or stopped at any position (for example, the position of the rotation axis (Z axis)) based on the control signal from the stage controlling unit 1717. The stage 1706 functions as a holding unit configured to hold the workpiece 1702 and be movable in the plane (in the XY plane) intersecting the rotation axis (Z axis).

The stage 1706 is configured to be movable according to the trajectory 1860 (shown in FIG. 18B) in the Φ direction around the rotation axis (Z axis) or a linear trajectory in the XY plane, for example. The stage 1706 can be positioned and stopped at a predetermined position in the XY plane based on the control signal from the stage controlling unit 1717. In other cases, the stage 1706 may be configured to arrange the workpiece 1702 at a position for examination by moving in one direction by a belt conveyor or the like.

The imaging apparatus controlling unit 1716 controls the position and the operation of the radiation imaging apparatus 1704. Further, the imaging apparatus controlling unit 1716 controls the moving positions of the robot arm 1705 and the imaging apparatus supporter 1703. The robot arm 1705 and the imaging apparatus supporter 1703 can move the radiation imaging apparatus 1704 to a specified position by moving the robot arm 1705 and the imaging apparatus supporter 1703 to a predetermined position based on the control signal from the imaging apparatus controlling unit 1716. For example, the robot arm 1705 and the imaging apparatus supporter 1703 may be configured as a moving mechanism that moves the radiation imaging apparatus 1704 with degrees of freedom in the XY direction and degrees of freedom in the rotation direction (Φ) around the Z axis (degrees of freedom in the XYΦ direction).

The radiation imaging apparatus 1704 is held in a predetermined position on the imaging apparatus supporter 1703. The imaging apparatus controlling unit 1716 obtains the position information of the imaging apparatus 1704 based on the moved positions of the robot arm 1705 and the imaging apparatus supporter 1703. The imaging apparatus controlling unit 1716 transmits the position information and the rotation angle information of the radiation imaging apparatus 1704 obtained based on the moved position and the rotation angle of the robot arm 1705 and the imaging apparatus supporter 1703 to the generating unit 1712.

The radiation imaging apparatus 1704 detects the radiation output by the radiation generating apparatus 1701 and transmitted through the workpiece 1702, and sends the image information of the projection image of the workpiece 1702 to the controlling unit 1710. The radiation imaging apparatus 1704 is configured to be movable in the plane intersecting the rotation axis (Z-axis) according to the operation of the robot arm 1705 and the imaging apparatus supporter 1703, which have the degree of freedom in the XYΦ direction, and detect the radiation transmitted through the object to be examined (the workpiece 1702). Here, the movement in the plane intersecting the rotation axis means, for example, a state where the radiation imaging apparatus 1704 moves in the plane (in the XY plane) intersecting the rotation axis (Z axis) with a predetermined trajectory 1850, as shown in FIG. 18A and FIG. 18B.

Here, the radiation imaging processing according to the third embodiment is described with reference to FIG. 18A and FIG. 18B. In the radiation imaging processing according to the third embodiment, in order to generate a three-dimensional image of the workpiece 1702 which is the object to be examined, a radiation is irradiated obliquely to the workpiece 1702 to image the plurality of projected images while changing the imaging position of the workpiece 1702.

FIG. 18A and FIG. 18B are diagrams for describing an example of the radiation imaging processing according to the third embodiment. FIG. 18A shows an example of the radiation imaging processing in a state where the radiation generating apparatus 1701 is moved in the plane (in the XY plane) intersecting the rotation axis (Z axis) with the predetermined trajectory 1840. On the other hand, FIG. 18B shows an example of the radiation imaging processing in a state where the radiation generating apparatus 1701 is stopped at the position of the rotation axis (Z axis). Note that the radiation imaging processing according to the third embodiment is not limited to the configurations shown in FIG. 18A and FIG. 18B. In the radiation imaging process according the third embodiment, it suffices to configure at least two of the radiation generating apparatus 1701, the stage 1706 for holding the object to be examined, and the radiation imaging apparatus 1704 to be movable in the plane intersecting the rotation axis (for example, to be rotated in conjunction with each other). Note that it suffices to configured the at least two to be movable in the plane intersecting the rotation axis so that the positional relationship in which the radiation irradiated from radiation generating apparatus 1701 transmits the object to be examined in a direction inclined to the rotation axis and can be detected by the radiation imaging apparatus 1704 is satisfied. For example, to satisfy the above-mentioned positional relationship, the radiation generating apparatus 1701, the stage 1706 and the radiation imaging apparatus 1704 may be configured to be movable in the plane intersecting the rotation axis. Alternatively, for example, to satisfy the above positional relationship, the radiation generating apparatus 1701 and the stage 1706 may be configured to be movable in the plane intersecting the rotation axis in a state where the radiation imaging apparatus 1704 is stopped at the position of the rotation axis.

Next, the image generation processing and the like in the control apparatus 1710 according to the third embodiment will be described. The obtaining unit 1711 obtains the image information transmitted from the radiation imaging apparatus 1704 and transmits the image information to the generating unit 1712. The obtaining unit 1711 may obtain a generated three-dimensional image and a tomographic image, which will be described later. Further, the obtaining unit 1711 may obtain these image information and various images from an external apparatus connected to the controlling apparatus 1710.

The generating unit 1712 generates a projection image using the image information received from the obtaining unit 1711. In this case, the generating unit 1712 can generate a high-energy image and a low-energy image in the same manner as the generating unit 132 according to the first and second embodiment, using the image information captured using the radiations of different energies. The radiation imaging operation using the radiations of different energies may be performed in the same manner as the radiation imaging described in the first embodiment. However, the radiation imaging operation according to the third embodiment is performed for each imaging positions of the workpiece 1702 by irradiating the radiation obliquely to the workpiece 1702 as described above in order to reconstruct the three-dimensional image from the projected images.

The generating unit 1712 can reconstruct the three-dimensional image from the plurality of projected images generated in such a manner. More specifically, the generating unit 1712 performs reconstruction processing using the position information and the rotation angle information of the radiation imaging apparatus 1704 received from the imaging apparatus controlling unit 1716 and the projected images of the workpiece 1702 captured by the radiation imaging apparatus 1704 to generate the three-dimensional image. Note that the generating unit 1712 can reconstruct the three-dimensional images of different energies using the projected images based on the radiations of different energies mentioned above.

Further, the generating unit 1712 can reconstruct a tomographic image of any cross-section from the generated three-dimensional image. Any known method may be used as the method for reconstructing the three-dimensional image and tomographic image. Here, a cross-section for cutting out the tomographic image from the three-dimensional image may be set based on the predetermined initial settings or according to an instruction from the operator. Further, the cross-section may be set automatically by the control device 1710 based on the detection result of the state of the object to be examined detected based on the projected image, information from various sensors (not shown) or the like, or according to selection of the examination purpose based on the operation by the operator. Note that in the third embodiment, the generating unit 1712 reconstructs tomographic images for three cross-sections, for example, an XY cross-section, a YZ cross-section and an XZ cross-section.

The processing unit 1713 can reconstruct a plurality of tomographic images relating to different radiation energies from the plurality of projection images relating to different radiation energies. Further, the processing unit 1713 can obtain at least one of energy-subtraction images with high image-quality as an output of an image-quality improving model by inputting the plurality of reconstructed tomographic images corresponding to different energies as input data of the image-quality improving model. The plurality of reconstructed tomographic images corresponding to different energies may be input to a respective plurality of channels of input data of the image-quality improving model. Here, in a case where the workpiece 1702 is a substrate or the like, the energy-subtraction images may be an image of the thickness of a metal such as a solder layer and an image of the thickness of an object other than the metal layer. Furthermore, the processing unit 1713 can perform various types of image processing in the same manner as the processing unit 133 according to the first and second embodiments.

Here, for the training data of the image-quality improving model according to the third embodiment, a plurality of tomographic images corresponding to different energies may be used as the input data and an energy-subtraction image with high image-quality may be used as the output data. For the plurality of tomographic image used as input data, a tomographic image obtained by imaging with a low dose may be used. Further, a tomographic image generated by adding an artificial noise to a tomographic image with high image-quality may be used as the input data. A tomographic image reconstructed from an image obtained by adding an artificial noise to a projection image or a three-dimensional image with high-image-quality may be used as input data. The method of generating energy-subtraction image with high image-quality may be the same as in the first and second embodiments. Here, the linear attenuation coefficient of metals, etc., may also be obtained from databases of NIST and the like.

Further, the configuration of the image-quality improving model is not limited to the configuration in which a tomographic image is employed as the input data and an energy-subtraction image with high-image-quality is employed as the output data. Similarly to the example of the image-quality improving model described in the first and second embodiments, a tomographic image with low image-quality may be employed as the input data and a tomographic image with high image-quality may be employed as the output data. In this case, the processing unit 1713 can generate at least one of energy-subtraction images with high image-quality by performing the signal processing of the energy-subtraction processing on the tomographic images with high image-quality output from the image-quality improving model. Note that the processing unit 1713 may perform the image-quality improvement on tomographic images corresponding to different energies by using one image-quality improving model or on each of a plurality of tomographic images corresponding to different energies by using each one image-quality improving model.

In this case, for the training data, a tomographic image with low image-quality may be used as the input data and a tomographic image with high image-quality may be used as the output data. As tomographic image with high image-quality, a tomographic image obtained by performing the imaging with a high dose and the reconstruction may be used, or a tomographic image of which the image quality is improved by averaging processing, etc., may be used. Further, as a tomographic image with high image-quality, a tomographic image generated using a projection image or a three-dimensional image of which the image quality is improved by averaging processing, etc. may be used. For the tomographic image with low image-quality, it may be generated similarly to the example mentioned above.

Further, similarly to the example of the image-quality improving model described in the first and second embodiments, for the image-quality improving model, an energy-subtraction image generated from tomographic images with low image-quality may be employed as the input data and an energy-subtraction image with high image-quality may be employed as the output data. In this case, the processing unit 1713 generates an energy-subtraction image from the generated tomographic images. The processing unit 1713 can obtain the at least one of energy-subtraction images with high image-quality as the output data of the image-quality improving model by inputting the generated energy-subtraction image as the input data of the image-quality improving model. For the training data, an energy-subtraction image with low image-quality may be used as the input data and an energy-subtraction image with high image-quality may be used as the output data. The energy-subtraction image with low image-quality may be generated by performing the signal processing of the energy-subtraction processing on the aforementioned tomographic image with low image-quality. Further, the energy-subtraction image with high image-quality may be generated in the same manner as the above example.

Furthermore, similarly to the example of the image-quality improving model described in the second embodiment, for the image-quality improving model, a virtual monochromatic image transformed from energy-subtraction images generated from tomographic images with low image-quality may be employed as the input data. In this case, the processing unit 1713 generates energy-subtraction images from the generated tomographic images and transforms the generated energy-subtraction images into a plurality of virtual monochromatic images of different energies. The processing unit 1713 can obtain energy-subtraction image with high image-quality as the output data of the image-quality improving model by inputting the plurality of virtual monochromatic images as the input data of the image-quality improving model. Note that the output data of the image-quality improving model may be an energy-subtraction image with high image-quality or a virtual monochromatic image with high-image-quality similarly to the example of the image-quality improving model described in the second embodiment.

Further, similarly to the example of the image-quality improving model described in the second embodiment, a virtual monochromatic image, and a tomographic image with low image-quality or an energy-subtraction image with low image-quality may be combined and employed as the input data. In this case, the processing unit 1713 generates energy-subtraction images from the generated tomographic images and transforms the generated energy-subtraction images into the plurality of virtual monochromatic images of different energies. The processing unit 1713 can obtain at least one of energy-subtraction images with high image-quality as the output data of the image-quality improving model by inputting the tomographic image or the energy-subtraction image and the plurality of virtual monochromatic images as the input data of the image-quality improving model. Further, the processing unit 1713 may obtain a tomographic image with high image-quality as the output data of the image-quality improving model by inputting a tomographic image or an energy-subtraction image and the plurality of virtual monochromatic images as the input data of the image-quality improving model. In this case, the processing unit 1713 can generate the at least one of energy-subtraction images with high-image-quality by performing the signal processing of the energy-subtraction processing on the obtained tomographic images with high image-quality.

Note that for the input data of the image-quality improving model, a tomographic image or an energy-subtraction image with low image-quality may be employed similarly to the example of the image-quality improving model described in the second embodiment. Further, for the output data of the image-quality improving model, a tomographic image or energy-subtraction image with high image-quality may be employed similarly to the example of the image-quality improving model described in the second embodiment. Note that the virtual monochromatic image may be generated in the same manner as in the method described in the second embodiment, except that the tomographic image is obtained by transforming the energy-subtraction images generated from a tomographic image. Further, the virtual monochromatic image with low image-quality and the virtual monochromatic image with high image-quality may be generated in the same manner as in the method described for the training data in the second embodiment.

The display controlling unit 1714 can cause the display unit 1720 to display energy-subtraction images with high image-quality and the like generated by the processing unit 1713. In a case where energy-subtraction images with high image-quality have been generated with respect to tomographic images for a plurality of cross-sections, the display controlling unit 1714 can cause the display unit 1720 to display these images side by side or switch each of these images to be displayed. Further, the display controlling unit 1714 may switch the display between the energy-subtraction images with high image-quality and the energy-subtraction images with low image-quality obtained by performing the energy-subtraction processing on the original tomographic image of different energies. In this case, the display controlling unit 1714 may collectively switch the display of these images according to an instruction from the operator via input unit 1750. In a case where the virtual monochromatic image or the DSA image are generated by the image processing, the display controlling unit 1714 can cause the display unit 1720 to display the generated virtual monochromatic image or DSA image.

Note that a series of imaging processes according to the third embodiment is omitted is similar to the series of imaging processes according to the first and second embodiments, and thus the description thereof is omitted. However, note that in the third embodiment, while the radiation imaging changes the imaging position of the workpiece 1702 as described above, the radiation is irradiated obliquely to the workpiece 1702 to capture the plurality of projected images. Further, note that in the third embodiment, the tomographic images corresponding to different energies are used to generate the at least one of energy-subtraction images.

As described above, the obtaining unit 1711 according to the third embodiment functions as an example of an obtaining unit that obtains a plurality of images obtained by irradiating radiations of different energies in an inclined direction with respect to an object to be examined. The plurality of images includes a plurality of tomographic images reconstructed from a plurality of projected images. Even in such a configuration, at least one of energy-subtraction images with high image-quality can be generated by using different energy images captured with low doses. Thus, the energy-subtraction with high image-quality image can be generated while reducing the radiation dose used for examination.

The controlling apparatus 1710 according to the third embodiment further includes a display controlling unit 1714 that causes the display unit 1720 to display the at least one of energy-subtraction images generated by the processing unit 1713. Further, the processing unit 1713 may generate a plurality of energy-subtraction images based on a plurality of tomographic images corresponding to at least two cross-sections of the object to be examined by using the image-quality improving model. The display controlling unit 1714 may cause the display unit 1720 to display the generated plurality of energy-subtraction images side-by-side. In this case, the energy-subtraction images relating to the plurality of cross-sections can be confirmed, and the examination for the object to be examined can be performed more efficiently.

Furthermore, the display controlling unit 1714 can cause the display unit 1720 to collectively switch, according to an instruction from the operator, the display between at least one of energy-subtraction images generated from a plurality of tomographic images corresponding to at least two cross-sections without using the image-quality improving model and the plurality of energy-subtraction images generated using image-quality improving model. In this case, it is possible to easily check whether artifact and the like have occurred by the processing using the image-quality improving model, and check how it is shown in the actually-captured image with respect to a site where abnormality may be occurred. Therefore, the examination on the object to be examined can be performed more efficiently.

Note that the cross-sections for the plurality of tomographic images can be set according to at least one of the initial settings, an instruction from the operator, the detection result of the state of the object to be examined, and the selection of the examination purpose. Thus, the tomographic images of cross-sections corresponding to the desired setting can be generated, and at least one of energy-subtraction images with high image-quality corresponding to the tomographic images can be generated. Thus, the examination on the object to be examined can be performed more efficiently.

The obtaining unit 1711 may function as an example of an obtaining unit that obtains a first image obtained by irradiating a radiation in a direction inclined with respect to the object to be examined. The processing unit 1713 may function as an example of a generating unit that obtains, by inputting the first image as the input data of the image-quality improving model, a second image with higher image-quality than the first image as the output data from the image-quality improving model, and generates at least one of energy-subtraction images using the second image. Even in such a configuration, at least one of energy-subtraction images with high image-quality can be generated by using different energy images captured with low doses. Thus, the at least one of energy-subtraction images with high image-quality can be generated while reducing the radiation dose used for examination.

Note that in the third embodiment, the processing unit 1713 generates the at least one of energy-subtraction images with high image-quality based on the plurality of tomographic images corresponding to different energies by using the image-quality improving model. In contrast, the processing unit 1713 may generate the at least one of energy-subtraction images with high image-quality based on projection images or three-dimensional images of different energies. In this case, projection images or three-dimensional images of different energies may be used as the input data of the training data of the image-quality improving model. Further, as the output data of training data, an energy-subtraction image corresponding to projection images or three-dimensional images of different energies may be used. Note that in a case where the three-dimensional images of different energies are used as the input data of the training data, an energy-subtraction image with high image-quality corresponding to a tomographic image of a predetermined cross-section may be used as the output data of the training data. Further, a projection image or a three-dimensional image may be used instead of a tomographic image for the above other examples in the image-quality improving model.

(Modification 1)

In the first and second embodiments, the image of the thickness of bone and the image of the thickness of soft tissue were described as the energy-subtraction images. On the other hand, an image of an effective atomic number Z and an image of area density D may be obtained from a low-energy image $Im_L$ and a high-energy image $Im_H$ as the energy-subtraction images. The effective atomic number Z is the atomic number equivalent to the mixture, and the area density D is the product of the density of the subject (g/cm3) and the thickness of the subject (cm).

First, in a case where the energy of a radiation photon is represented as E, the number of photons at energy E is represented as N(E), the effective atomic number is represented as Z, the area density is represented as D, the mass attenuation coefficient relating to the effective atomic number Z and the energy E is represented as μ(Z, E), and the attenuation ratio is represented as $I/I_0$, the following equation (14) is satisfied.

$$\frac{I}{I_0} = \frac{\int_0^\infty N(E)\exp\{-\mu_B(Z, E)D\}EdE}{\int_0^\infty N(E)EdE} \tag{14}$$

The photon number N(E) at the energy E is the spectrum of the radiation. The spectrum of the radiation can be obtained by simulation or by actual measurement. Further, the mass attenuation coefficient μ(Z, E) relating to the effective atomic number Z and the energy E is obtained from the databases of NIST or the like. Therefore, it is possible to calculate the attenuation ratio $I/I_0$ relating to any effective atomic number Z, any area density D, and any spectrum N(E) of the radiation.

In a case where the spectrum for X-rays with a low-energy is represented as $N_L(E)$ and the spectrum for X-rays with a high-energy is represented $N_H(E)$, the following equation (15) is satisfied.

$$L = \frac{\int_0^\infty N_L(E)\exp\{-\mu_B(Z, E)D\}EdE}{\int_0^\infty N_L(E)EdE} \tag{15}$$
$$H = \frac{\int_0^\infty N_H(E)\exp\{-\mu_B(Z, E)D\}EdE}{\int_0^\infty N_H(E)EdE}$$

Equation (15) is nonlinear simultaneous equations. The controlling apparatus 103 can calculate an image indicating the effective atomic number Z and an image indicating the area density D from a low-energy image $Im_L$ and a high-energy image $Im_H$ by solving the equation (15) by the Newton-Raphson method or the like. It is also possible to generate a virtual monochromatic image using the effective atomic number Z and the area density D after calculating the effective atomic number Z and the area density D.

According to such image processing of the energy-subtraction processing, an image of the effective atomic number Z and an image of the area density D can be obtained from the low-energy image $Im_L$ and the high-energy image $Im_H$ as energy-subtraction images. Therefore, such an image of the effective atomic number Z and an image of the area density D can be used as the energy-subtraction image for the training data, the input data and/or the output data of the image-quality improving model. In this case, the image of the effective atomic number Z and the image with the area density D can be generated and obtained as the energy-subtraction images instead of the bone image and the soft tissue image with respect to the above-described embodiments. Further, an image of the effective atomic number Z with high image-quality and an image of the area density D with high-image-quality can be obtained by performing the energy-subtraction processing on the energy images with high-image-quality.

(Modification 2)

In the above-described first to third embodiments, the radiation imaging apparatus 104 is an indirect-type X-ray sensor using a scintillator. However, the present disclosure is not limited to such a configuration. For example, a direct-type X-ray sensor using a direct-conversion material such as CdTe may be used.

In the above-described first to third embodiments, the radiation images of different energies are obtained by changing the tube voltage of the radiation generating apparatus 101, etc. However, the present disclosure is not limited to such a configuration. The energy of X-rays irradiated to the radiation imaging apparatus 104 may be changed by switching the filter of the radiation generating apparatus 101 in time, and the like. Further, by piling a plurality of the scintillators 105 and a plurality of the two-dimensional detectors 106, the images of different energies may be obtained from a two-dimensional detector in the front stage and a two-dimensional detector in the rear stage with respect to the incident direction of the X-rays. Furthermore, the images of different energies may be obtained by single imaging by using a plurality of different scintillators 105 and a plurality of different two-dimensional detectors 106. In addition, the images of different energies may be obtained from single imaging by providing a light-shielding portion in a part of the two-dimensional detector 106.

In the above-described first to third embodiments, the configuration using the radiation imaging apparatus 104, 1704 including the pixels 20 shown in FIG. 2 is described. However, the configuration of the pixels of the radiation imaging apparatus 104, 1704 is not limited to this and may be freely designed according to the desired configuration.

(Modification 3)

Furthermore, the training data of the learned model according to the above-described first to third embodiments and modifications is not limited to data obtained using the radiation imaging apparatus that itself performs the actual imaging. The training data may be data obtained using a radiation imaging apparatus of the same model, or data obtained using a radiation imaging apparatus of the same type or the like, depending on the desired configuration.

In the above-described first to third embodiments and modifications, the plurality of input images is input to the respective plurality of input channels of the image-quality improving model. In contrast, the plurality of input images may be combined into single image, and the single image may be input to one channel of the image-quality improving model. In this case, a single image into which the input images are combined may be used as the input data for the training data of the image-quality improving model, similarly.

Note that in the learned model according to the above-described first to third embodiments and modifications, it is conceivable for the magnitude of luminance values of the image as the input data, as well as the order, slope, position, distribution, and continuity of the bright sections and dark sections and the like of the image as the input data to be extracted as part of the feature amount and used for inference processing.

Further, various learned models according to the above-described first to third embodiments and modification can be provided in the control apparatus 103 or 1710. The learned models may be constituted by, for example, a software module executed by a processor such as a CPU, an MPU, a GPU or an FPGA, or may be constituted by a circuit that serves a specific function such as an ASIC. Further, the learned models may be provided in different device such as a server or the like which is connected to the controlling apparatuses 103 or 1710. In this case, the controlling apparatus 103 or 1710 can use the learned model by connecting to the server or the like that includes the learned model through any network such as the Internet. Here, the server that includes learned model may be, for example, a cloud server, a FOG server, an edge server or the like. Note that, in a case where a network within the facility, or within premises in which the facility is included, or within an area in which a plurality of facilities is included or the like is configured to enable wireless communication, for example, the reliability of the network may be improved by configuring the network to use radio waves in a dedicated wavelength band allocated to only the facility, the premises, or the area or the like. Further, the network may be constituted by wireless communication that is capable of high speed, large capacity, low delay, and many simultaneous connections.

According to the above-described first to third embodiments and modifications, at least one of energy-subtraction images with high image-quality can be generated while reducing the radiation dose used for examination.

(Other Embodiments)

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

In this case, the processor or circuit may include a central processing unit (CPU), a microprocessing unit (MPU), a graphics processing unit (GPU), an application specific integrated circuit (ASIC), or a field programmable gateway (FPGA). Further, the processor or circuit may include a digital signal processor (DSP), a data flow processor (DFP) or a neural processing unit (NPU).

The present disclosure includes the following configurations, methods, and a program.

(Configuration 1)

An imaging apparatus comprising:

an obtaining unit configured to obtain a plurality of images relating to different radiation energies; and a generating unit configured to generate at least one of energy-subtraction images based on the plurality of images using a learned model, wherein the learned model is obtained using a first image obtained using a radiation and a second image obtained by improving image-quality of the first image.

(Configuration 2)

The image processing apparatus according to the configuration 1, wherein the second image is either an image obtained using a dose higher than a dose used to obtain the first image, or an image obtained by performing averaging processing or estimation processing of maximum a posteriori using the first image.

(Configuration 3)

An image processing apparatus comprising:

an obtaining unit configured to obtain a plurality of images relating to different radiation energies; and a generating unit configured to generate at least one of energy-subtraction images based on the plurality of images using a learned model, wherein the learned model is obtained using a first image obtained using a radiation and a second image obtained by adding a noise which has been artificially calculated to the first image.

(Configuration 4)

The image processing apparatus according to any one of the configurations 1-3, wherein the generating unit is configured to obtain, by inputting the plurality of images as input data of the learned model, the at least one of energy-subtraction images as output data from the learned model.

(Configuration 5)

An image processing apparatus comprising:

an obtaining unit configured to obtain a plurality of images relating to different radiation energies; and a generating unit configured to obtain, by inputting the plurality of images as input data of a learned model, at least one of energy-subtraction images as output data from the learned model.

(Configuration 6)

The image processing apparatus according to any one of the configurations 1-3, wherein the generating unit is configured to:

obtain, by inputting the plurality of images as input data of the learned model, a plurality of images with higher image-quality than the plurality of images as output data from the learned model; and generate the at least one of energy-subtraction images from the plurality of images obtained as the output data from the learned model.

(Configuration 7)

The image processing apparatus according to any one of the configurations 1-3, wherein the generating unit is configured to:

generate at least one of first energy-subtraction images from the plurality of images; and obtain, by inputting the at least one of first energy-subtraction images as input data of the learned model, at least one of second energy-subtraction images with higher image-quality than the at least one of first energy-subtraction images as output data from the learned model.

(Configuration 8)

The image processing apparatus according to any one of the configurations 1-3, wherein the generating unit is configured to:

generate first energy-subtraction images from the plurality of images;

generate a plurality of virtual monochromatic images of different energies from the first energy-subtraction images; and generate at least one of second energy-subtraction images with higher image-quality than the first energy-subtraction images based on the plurality of virtual monochromatic images using the learned model.

(Configuration 9)

The image processing apparatus according to the configuration 8, wherein the generating unit is configured to obtain, by inputting the plurality of virtual monochromatic images as input data of the learned model, the at least one of second energy-subtraction images as output data from the learned model.

(Configuration 10)

The image processing apparatus according to the configuration 8, wherein the generating unit is configured to:

obtain, by inputting the plurality of virtual monochromatic images as input data of the learned model, a plurality of virtual monochromatic images with higher image-quality than the generated plurality of virtual monochromatic images as output data from the learned model; and generate the at least one of second energy-subtraction images from the plurality of virtual monochromatic images obtained as the output data from the learned model.

(Configuration 11)

The image processing apparatus according to any one of the configurations 1-3, wherein the generating unit is configured to:

generate first energy-subtraction images from the plurality of images;

generate a virtual monochromatic image from the first energy-subtraction images; and obtain, by inputting the plurality of images and the virtual monochromatic image as input data of the learned model, at least one of second energy-subtraction images with higher image-quality than the first energy-subtraction images as output data from the learned model.

(Configuration 12)

The image processing apparatus according to any one of the Configurations 1-3, wherein the generating unit is configured to:

generate first energy-subtraction images from the plurality of images;

generate a virtual monochromatic image from the first energy-subtraction images;

obtain, by inputting the plurality of images and the virtual monochromatic image as input data of the learned model, a plurality of images with higher image-quality than the obtained plurality of images as output data from the learned model; and generate at least one of second energy-subtraction images with higher image-quality than the first energy-subtraction images from the plurality of images obtained as the output data from the learned model.

(Configuration 13)

The image processing apparatus according to any one of the configurations 1-3, wherein the generating unit is configured to:

generate first energy-subtraction images from the plurality of images;

generate a virtual monochromatic image from the first energy-subtraction images; and obtain, by inputting the virtual monochromatic image and at least one of the first energy-subtraction images as input data of the learned model, at least one of second energy-subtraction images with higher image-quality than the first energy-subtraction images as output data from the learned model.

(Configuration 14)

The image processing apparatus according to any one of the configurations 1-3, wherein the learned model has a plurality of input channels into which a respective plurality of images is input.

(Configuration 15)

The image processing apparatus according to the configuration 6, wherein the learned model includes a plurality of learned models corresponding to the respective plurality of images used as the input data of the learned model.

(Configuration 16)

The image processing apparatus according to the configuration 10, wherein the learned model includes a plurality of learned models corresponding to the respective plurality of virtual monochromatic images used as the input data of the learned model.

(Configuration 17)

The image processing apparatus according to any one of the configurations 1-16, wherein the at least one of energy-subtraction images includes a plurality of material decomposition images discriminating a plurality of materials and a respective plurality of images indicating an effective atomic number and area density.

(Configuration 18)

The image processing apparatus according to the configuration 17, wherein the plurality of material decomposition images includes an image indicating thickness of bone and an image indicating thickness of soft tissue, an image indicating thickness of a contrast medium and an image indicating thickness of water, and an image indicating metal and an image in which metal is removed.

(Configuration 19)

The image processing apparatus according to the configuration 18, wherein the generating unit is configured to calculate bone density using the image indicating the thickness of bone and the image indicating the thickness of soft tissue.

(Configuration 20)

The image processing apparatus according to any one of the configurations 1-19, wherein:

the obtaining unit is configured to obtain a plurality of images obtained by irradiating radiations of different energies in an inclined direction with respect to an object to be examined; and the plurality of images includes a plurality of projection images or a plurality of tomographic images reconstructed from the plurality of projection images.

(Configuration 21)

The image processing apparatus according to the configuration 20, further comprising a display controlling unit configured to cause a display unit to display the at least one of energy-subtraction images generated by the generating unit, wherein:

the generating unit is configured to generate, using the learned model, a plurality of energy-subtraction images based on a plurality of tomographic images corresponding to at least two cross-sections of the object to be examined; and the display controlling unit is configured to cause the display unit to display the plurality of energy-subtraction images side by side.

(Configuration 22)

The image processing apparatus according to the configuration 21, wherein the display controlling unit is configured to cause the display unit to collectively switch, according to an instruction from an operator, display between at least one of energy-subtraction images generated from a plurality of tomographic images corresponding to the at least two cross-sections without using the learned model and the plurality of energy-subtraction images generated using the learned model.

(Configuration 23)

The image processing apparatus according to any one of the configurations 20-22, wherein cross-sections relating to the plurality of tomographic images is set according to at least one of an initial setting, an instruction from an operator, a detection result of a state of the object to be examined, and selection of an examination purpose.

(Configuration 24)

An image processing apparatus comprising:

an obtaining unit configured to obtain a plurality of first images relating to different radiation energies; and a generating unit configured to obtain, by inputting the plurality of first images as input data of a learned model, a plurality of second images with higher image-quality than the plurality of first images as output data from the learned model, and generate at least one of energy-subtraction images using the plurality of second images.

(Configuration 25)

The image processing apparatus comprising:

an obtaining unit configured to obtain a first image obtained by irradiating a radiation in an inclined direction with respect to an object to be examined; and a generating unit configured to obtain, by inputting the first image as input data of a learned model, a second image with higher image-quality than the first image as output data from the learned model, and generate at least one of energy-subtraction images using the second image.

(Method 1)

An image processing method comprising:

obtaining a plurality of images relating to different radiation energies; and generating at least one of energy-subtraction images based on the plurality of images by using a learned model, wherein the learned model is obtained using a first image obtained using a radiation and a second image obtained by improving image-quality of the first image.

(Method 2)

An image processing method comprising:

obtaining a plurality of images relating to different radiation energies; and generating at least one of energy-subtraction images based on the plurality of images using a learned model, wherein the learned model is obtained using a first image obtained using a radiation and a second image obtained by adding a noise which has been artificially calculated to the first image.

(Method 3)

An image processing method comprising:

obtaining a plurality of images relating to different radiation energies; and obtaining, by inputting the plurality of images as input data of a learned model, at least one of energy-subtraction images as output data from the learned model.

(Method 4)

An image processing method comprising:

obtaining a plurality of first images relating to different radiation energies; and obtaining, by inputting the plurality of first images as input data of a learned model, a plurality of second images with higher image-quality than the plurality of first images as output data from the learned model, and generating at least one of energy-subtraction images using the plurality of second images.

(Method 5)

An image processing method comprising:

obtaining a first image obtained by irradiating a radiation in an inclined direction with respect to an object to be examined; and obtaining, by inputting the first image as input data of a learned model, a second image with higher image-quality than the first image as output data from the learned model, and generating at least one of energy-subtraction images using the second image.

(Computer-Readable Medium 1)

A non-transitory computer-readable medium having stored thereon a program that, when executed by a computer, causes the computer to execute respective steps of the image processing method of any one of the methods 1-5.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-023949, filed Feb. 18, 2022 which is hereby incorporated by reference herein in its entirety.

What is claimed is:

1. An image processing apparatus comprising:

at least one processor; and a memory coupled to the at least one processor, the memory having instructions that, when executed by the processor, causes the at least one processor to:

obtain a plurality of images relating to different radiation energies; and generate a pair of an image indicating thickness of bone and an image indicating thickness of soft tissue as first energy-subtraction images based on the plurality of images;

generate a plurality of virtual monochromatic images of different energies from the first energy-subtraction images; and generate a pair of an image indicating thickness of bone and an image indicating thickness of soft tissue as second energy-subtraction images with reduced noise than the first energy-subtraction images based on the plurality of virtual monochromatic images using a learned model, wherein the learned model is obtained using a first image obtained using a radiation and a second image obtained by performing noise reduction processing on the first image or by adding a noise which has been artificially calculated to the first image.

2. The image processing apparatus according to claim 1, wherein the second image is either an image obtained using a dose higher than a dose used to obtain the first image, or an image obtained by performing averaging processing or estimation processing of maximum a posteriori using the first image.

3. The image processing apparatus according to claim 1, wherein the instructions when executed further cause the at least one processor to obtain, by inputting the plurality of virtual monochromatic images into the learned model, the second energy-subtraction images as output data from the learned model.

4. The image processing apparatus according to claim 1, wherein the instructions when executed further cause the at least one processor to: calculate bone density using the image indicating the thickness of bone and the image indicating the thickness of soft tissue.

5. An image processing method comprising:

obtaining a plurality of images relating to different radiation energies;

generating a pair of an image indicating thickness of bone and an image indicating thickness of soft tissue as first energy-subtraction images based on the plurality of images;

generating a plurality of virtual monochromatic images of different energies from the first energy-subtraction images; and generating a pair of an image indicating thickness of bone and an image indicating thickness of soft tissue as second energy-subtraction images with reduced noise than the first energy-subtraction images based on the plurality of virtual monochromatic images using a learned model, wherein the learned model is obtained using a first image obtained using a radiation and a second image obtained by performing noise reduction processing on the first image or by adding a noise which has been artificially calculated to the first image.

6. A non-transitory computer-readable medium having stored thereon a program that, when executed by a computer, causes the computer to execute respective steps of the image processing method of claim 5.

* * * * *